(12) United States Patent
Pelc et al.

(10) Patent No.: US 6,422,431 B2
(45) Date of Patent: Jul. 23, 2002

(54) MICROVOLUME LIQUID HANDLING SYSTEM

(75) Inventors: Richard E. Pelc, Libertyville; Nicholas S. Chibucos, Bloomingdale, both of IL (US); Roeland F. Papen, Guilford, CT (US); Wilhelm Meyer, Tostedt (DE)

(73) Assignee: Packard Instrument Company, Inc., Downers Grove, IL (US)

( * ) Notice: Subject to any disclaimer, the term of this patent is extended or adjusted under 35 U.S.C. 154(b) by 0 days.

(21) Appl. No.: 09/775,229

(22) Filed: Feb. 1, 2001

Related U.S. Application Data

(60) Division of application No. 09/056,233, filed on Apr. 7, 1998, now Pat. No. 6,203,759, which is a continuation-in-part of application No. 08/656,455, filed on May 31, 1996, now abandoned.
(60) Provisional application No. 60/067,665, filed on Dec. 5, 1997, and provisional application No. 60/041,861, filed on Apr. 8, 1997.

(51) Int. Cl.[7] .................................................. B01L 3/02
(52) U.S. Cl. ........................... 222/422; 222/1; 222/420
(58) Field of Search ................................ 222/420, 422, 222/1

(56) References Cited

U.S. PATENT DOCUMENTS

| | | | |
|---|---|---|---|
| 3,427,480 A | 2/1969 | Robinson | |
| 3,452,360 A | 6/1969 | Williamson | |
| 3,507,269 A | 4/1970 | Berry | |

(List continued on next page.)

FOREIGN PATENT DOCUMENTS

| | | |
|---|---|---|
| DE | 3 007 189 | 11/1980 |
| DE | 3 014 256 | 12/1980 |
| DE | 3 332 491 | 3/1985 |
| DE | 3 833 586 | 7/1989 |
| DE | 3 915 920 | 11/1990 |
| DE | 4 140 533 | 6/1993 |
| DE | 0 301 771 | 11/1993 |
| DE | 19 532382 | 3/1997 |
| EP | 0 012 821 | 11/1979 |

(List continued on next page.)

OTHER PUBLICATIONS

Ashley et al. "Development and Characterization of Ink for an Electrostatic Ink Jet Printer" pp. 69–74, IBM J. Res. Develop.
Beach et al., "Materials Selection for an ink Jet Printer" pp. 75–86, IBM J. Res. Develop.

(List continued on next page.)

Primary Examiner—J. Casimer Jacyna
(74) Attorney, Agent, or Firm—Jenkens & Gilchrist

(57) ABSTRACT

In one embodiment, a microvolume liquid handling system includes a microdispenser employing a piezoelectric transducer attached to a glass capillary, a positive displacement pump for priming and aspiring transfer liquid into the microdispenser, controlling the pressure of the liquid system and washing the microdispenser between liquid transfers, and a pressure sensor to measure the liquid system pressure and produce a corresponding electrical signal. The pressure signal is used to verify and quantify the microvolume of transfer liquid dispensed and is used to perform automated calibration and diagnostics on the microdispenser. In another embodiment of the microvolume liquid handling system, a system reservoir is connected with tubing to a pressure control system for controlling the liquid system pressure in the system reservoir. The system reservoir is coupled to one or more microdispenser through a distribution tube having a branched section for each microdispenser. In this embodiment, each microdispenser is coupled to its own flow sensor and which enables a system controller to respectively measure and control the flow of liquid in each dispenser.

4 Claims, 12 Drawing Sheets

U.S. PATENT DOCUMENTS

| | | |
|---|---|---|
| 3,512,173 A | 5/1970 | Darmouth |
| 3,549,328 A | 12/1970 | Kilburn |
| 3,666,421 A | 5/1972 | Price |
| 3,683,212 A | 8/1972 | Zoltan |
| 3,711,252 A | 1/1973 | Roy |
| 3,798,961 A | 3/1974 | Flambard et al. |
| 3,831,845 A | 8/1974 | Packt |
| 3,832,579 A | 8/1974 | Arndt |
| 3,838,012 A | 9/1974 | Higgens |
| 3,859,169 A | 1/1975 | O'Driscoll et al. |
| 3,902,083 A | 8/1975 | Zoltan |
| 3,946,398 A | 3/1976 | Kyser et al. |
| 3,958,249 A | 5/1976 | DeMaine et al. |
| 3,964,871 A | 6/1976 | Hochstrasser |
| 3,975,162 A | 8/1976 | Renn |
| 3,985,467 A | 10/1976 | Lefferson |
| 3,994,423 A | 11/1976 | Burg |
| 3,996,006 A | 12/1976 | Pagano |
| 4,038,570 A | 7/1977 | Durley, III |
| 4,046,513 A | 9/1977 | Johnson |
| 4,084,165 A | 4/1978 | Skafvensted et al. |
| 4,087,332 A | 5/1978 | Hansen |
| 4,193,009 A | 3/1980 | Durley, III |
| 4,216,245 A | 8/1980 | Johnson |
| 4,223,558 A | 9/1980 | Schmider et al. |
| 4,234,103 A | 11/1980 | Strobl, Jr. et al. |
| 4,241,406 A | 12/1980 | Kennedy et al. |
| 4,278,983 A | 7/1981 | Halasz |
| 4,293,867 A | 10/1981 | Isayama |
| 4,308,546 A | 12/1981 | Halasz |
| 4,341,310 A | 7/1982 | Sangiovanni et al. |
| 4,366,490 A | 12/1982 | DeBonte et al. |
| 4,410,020 A | 10/1983 | Lorenz ........................ 141/65 |
| 4,418,356 A | 11/1983 | Reece |
| 4,426,031 A | 1/1984 | Halasz |
| 4,447,375 A | 5/1984 | Schimmelpfennig |
| 4,492,322 A | 1/1985 | Hieftje et al. |
| 4,498,088 A | 2/1985 | Kanayama |
| 4,503,012 A | 3/1985 | Starr |
| 4,504,845 A | 3/1985 | Kattner et al. |
| 4,512,722 A | 4/1985 | Mouton |
| 4,514,743 A | 4/1985 | Roschlein et al. |
| 4,518,974 A | 5/1985 | Isayama |
| 4,530,463 A | 7/1985 | Hiniker et al. |
| 4,539,575 A | 9/1985 | Nilsson |
| 4,548,825 A | 10/1985 | Voss et al. |
| 4,550,325 A | 10/1985 | Viola |
| 4,600,928 A | 7/1986 | Braun et al. |
| 4,633,413 A | 12/1986 | Bailey et al. |
| 4,646,104 A | 2/1987 | Braun |
| 4,651,161 A | 3/1987 | Rich et al. |
| 4,672,398 A | 6/1987 | Kuwabara et al. |
| 4,681,741 A | 7/1987 | Hanaway |
| 4,682,710 A | 7/1987 | Turner, Jr. et al. |
| 4,691,850 A | 9/1987 | Kirschmann et al. ........ 222/642 |
| 4,695,852 A | 9/1987 | Scardovi |
| 4,701,754 A | 10/1987 | Provonchee |
| 4,777,832 A | 10/1988 | Prodosmo et al. |
| 4,877,745 A | 10/1989 | Hayes et al. |
| 4,934,419 A | 6/1990 | Lamont et al. ................ 141/94 |
| 4,976,259 A | 12/1990 | Higson et al. |
| 5,039,614 A | 8/1991 | Dekmezian et al. |
| 5,055,263 A | 10/1991 | Meltzer |
| 5,059,393 A | 10/1991 | Quenin et al. |
| 5,072,235 A | 12/1991 | Slowik et al. |
| 5,141,871 A | 8/1992 | Kureshy et al. |
| 5,225,750 A | 7/1993 | Higuchi et al. |
| 5,229,679 A | 7/1993 | Higuchi et al. |
| 5,232,664 A | 8/1993 | Krawzak et al. |
| 5,297,734 A | 3/1994 | Toda |
| 5,306,510 A | 4/1994 | Meltzer |
| 5,334,353 A | 8/1994 | Blattner |
| 5,356,034 A | 10/1994 | Schlumberger |
| 5,365,783 A | 11/1994 | Zweifel |
| 5,415,679 A | 5/1995 | Wallace |
| 5,449,345 A | 9/1995 | Taylor et al. |
| 5,453,091 A | 9/1995 | Taylor et al. |
| 5,457,527 A | 10/1995 | Manns et al. |
| 5,485,828 A | 1/1996 | Hauser |
| 5,525,515 A | 6/1996 | Blattner ........................ 436/49 |
| 5,529,754 A | 6/1996 | Bonacina et al. |
| 5,543,827 A | 8/1996 | VanSteenkiste et al. |
| 5,620,004 A | 4/1997 | Johansen |
| 5,630,793 A | 5/1997 | Rowe |
| 5,651,648 A | 7/1997 | Furey |
| 5,653,726 A | 8/1997 | Kieturakis |
| 5,655,446 A | 8/1997 | Watanabe |
| 5,658,723 A | 8/1997 | Oberhardt et al. |
| 5,658,802 A | 8/1997 | Hayes et al. |
| 5,659,173 A | 8/1997 | Putterman et al. |
| 5,661,245 A | 8/1997 | Svoboda et al. |
| 5,663,754 A | 9/1997 | Lorenze et al. |
| 5,673,073 A | 9/1997 | Childers et al. |
| 5,674,238 A | 10/1997 | Sample et al. |
| 5,675,367 A | 10/1997 | Scheffelin et al. |
| 5,681,757 A | 10/1997 | Hayes |
| 5,682,236 A | 10/1997 | Trolinger |
| 5,685,310 A | 11/1997 | Porter |
| 5,685,848 A | 11/1997 | Robinson et al. |
| 5,690,907 A | 11/1997 | Lanza et al. |
| 5,691,478 A | 11/1997 | Barry et al. |
| 5,693,016 A | 12/1997 | Gumaste et al. |
| 5,694,919 A | 12/1997 | Rubsamen et al. |
| 5,694,946 A | 12/1997 | Tenerz et al. |
| 5,695,457 A | 12/1997 | St. Goar et al. |
| 5,695,461 A | 12/1997 | Schaible |
| 5,695,468 A | 12/1997 | Lafontaine et al. |
| 5,695,740 A | 12/1997 | Porter |
| 5,697,375 A | 12/1997 | Hickey |
| 5,698,018 A | 12/1997 | Bishop et al. |
| 5,700,848 A | 12/1997 | Soon-Shiong et al. |
| 5,701,899 A | 12/1997 | Porter |
| 5,702,384 A | 12/1997 | Umeyama et al. |
| 5,763,278 A | 6/1998 | Sickinger et al. |
| 5,918,291 A * | 6/1999 | Inacu et al. ............. 73/863.83 |
| 5,927,547 A | 7/1999 | Papen et al. |

FOREIGN PATENT DOCUMENTS

| | | |
|---|---|---|
| EP | 0 024 230 | 2/1981 |
| EP | 0 072 558 | 2/1983 |
| EP | 0 119 573 | 9/1984 |
| EP | 0 169 071 | 1/1986 |
| EP | 0 202 022 | 11/1986 |
| EP | 0 219 177 | 4/1987 |
| EP | 0 268 237 | 5/1988 |
| EP | 0 412 431 | 2/1991 |
| EP | 0 432 992 | 6/1991 |
| EP | 0 438 136 | 7/1991 |
| EP | 0 446 972 | 9/1991 |
| EP | 0 508 531 | 10/1992 |
| EP | 0 513 441 | 11/1992 |
| EP | 0 545 284 | 6/1993 |
| EP | 0 548 872 | 6/1993 |
| EP | 0 568 024 | 11/1993 |
| EP | 0 581 708 | 2/1994 |
| EP | 0 628 413 | 12/1994 |
| EP | 0 655 256 | 5/1995 |
| EP | 0 712 232 | 5/1996 |
| EP | 0 718 046 | 6/1996 |
| EP | 0 747 689 | 12/1996 |
| EP | 0 761 256 | 3/1997 |

| | | |
|---|---|---|
| EP | 0 763 742 | 3/1997 |
| EP | 0 766 946 | 5/1997 |
| EP | 0 779 436 | 6/1997 |
| EP | 0 781 987 | 7/1997 |
| EP | 0 788 809 | 8/1997 |
| EP | 0 789 383 | 8/1997 |
| EP | 0 795 409 | 9/1997 |
| EP | 0 810 096 | 12/1997 |
| EP | 0 810 438 | 12/1997 |
| ES | 2073992 | 8/1995 |
| JP | 55-79167 | 12/1978 |
| JP | 1-038147 | 2/1989 |
| JP | 1-150549 | 6/1989 |
| JP | 01234144 | 9/1989 |
| JP | 2-017079 | 1/1990 |
| RU | 2011961 | 4/1994 |
| RU | 400042 | 8/1997 |
| SU | 0 783 635 | 11/1980 |
| SU | 0 791 954 | 12/1980 |
| SU | 0 858 845 | 9/1981 |
| SU | 1 089 420 | 4/1985 |
| SU | 1 262 376 | 10/1986 |
| SU | 1 436 057 | 11/1988 |
| SU | 1 740 007 | 6/1992 |
| WO | WO 89/00725 | 1/1989 |
| WO | WO 89/10193 | 11/1989 |
| WO | WO 90/11040 | 10/1990 |
| WO | WO 92/11050 | 7/1992 |
| WO | WO 92/15256 | 9/1992 |
| WO | WO 92/15361 | 9/1992 |
| WO | WO 92/18608 | 10/1992 |
| WO | WO 93/10910 | 6/1993 |
| WO | WO 94/06568 | 3/1994 |
| WO | WO 95/01559 | 1/1995 |
| WO | WO 95/04502 | 2/1995 |
| WO | WO 95/26236 | 10/1995 |
| WO | WO 95/35212 | 12/1995 |
| WO | WO 96/12609 | 5/1996 |
| WO | WO 97/16251 | 5/1997 |

OTHER PUBLICATIONS

Boillat et al., "A Differential Pressure Liquid Flow Sensor for Flow Regulation and Dosing Systems," Proceedings IEEE, Micro Electro Mechanical Systems, MEMS, '95 Amsterdam.

Buehner, et al., "Application of Ink Jet Technology to a Word Processing Output Printer", pp. 1–9, IBM J. Res. Develop.

Carmichael, "Controlling Print Height in an Ink Jet Printer" pp. 52–55, IBM J. Res. Develop.

Curry, Portig, "Scale Model of an Ink Jet", pp. 10–20, IBM J. Res. Develop.

Filmore et al. Drop Charging and Defection in an Electrostatic Ink Jet Printer, pp. 37–47 IBM J. Res. Develop.

Holcombe, Eklund & Grice, "Vaporization and Atomization of Large Particles in an Acetylene/Air Flame", pp. 2097–2103, Analytical Chemistry, vol. 50, No. 14, Dec. 1978.

Joshi and Sacks "Circular Slot Burner–Droplet Generator System for High–Temperature Reaction and Vapor Transport Studies", pp. 1781–1785, Analytical Chemistry, vol. 51, No. 11, Sep. 1979.

Lee "Boundary Layer Around a Liquid Jet" pp. 48–51, IBM J. Res. Develop.

Levanoni, "Study of Fluid Flow through Scaled–up Ink Jet Nozzles" pp. 56–68, IBM J. Res. Develop.

Microdrop Instruction Manual, Microdrop Gesellschaft für Mikrodosiersysteme mbH, MD–K–130SP/140H/135/150 and Drive electronics MD–E–204, May 1994.

Microdrop Instruction Manual, Microdrop Gesellschaft für Mikrodosiersysteme mbH, AD–E–130, Sep. 1995.

Microdrop Literature, "Flussigkeiten mikrofein dosieren" Gesellschaft for Mikrodosiersysteme mbH, 1994 (in the German language).

Microdrop literature, "Microdosing in the picoliter range with piezo technology" sales brochure from Microdrop Gesellschaft für Mickrodosiersysteme mbH, Oct., 1995.

Pimbley "Satellite Droplet Formation in a Liquid Jet" pp. 21–30, Satellite Formation, IBM J. Res. Develop.

Plunkett, Matthew J. et al., "Combinatorial Chemistry and New Drugs," Scientific American, Apr. 1997, pp. 69–73.

Schober, A., et al., "Accurate High–Speed Liquid Handling of Very Small Biological Samples," BioTechniques, vol. 15, No. 2 (1993), pp. 324–329.

Twardeck "Effect of Parameter Variations on Drop Placement in an Electrostatic Ink Jet Printer" pp. 31–36, IBM J. Res. Develop.

Zengerle et al., "Carbon Dioxide Priming of Micro Liquid Systems," *IEEE* (1995), pp. 340–343.

* cited by examiner

MICROVOLUME LIQUID HANDLING SYSTEM

RELATED APPLICATIONS

This patent application is a division of U.S. application Ser. No. 09/056,233 filed Apr. 7, 1998, now U.S. Pat. No. 6,203,759 which is a continuation-in-part application of a pending U.S. patent application Ser. No. 08/656,455, filed May 31, 1996, now abandoned, a pending provisional U.S. patent application Ser. No. 60/041,861 filed Apr. 8, 1997, and a pending provisional U.S. patent application Ser. No. 60/067,665 filed Dec. 5, 1997.

FIELD OF THE INVENTION

The present invention relates to an apparatus and process for controlling, dispensing and measuring small quantities of liquids. More specifically, the present invention senses pressure changes to ascertain and confirm the volume dispensed liquids and proper system functioning. In particular, the present invention relates to aspirating and dispensing picoliter range droplets of liquid.

BACKGROUND OF THE INVENTION

Advances in industries employing chemical and biological processes have created a need for the ability to accurately and automatically dispense small quantities of liquids containing chemically or biologically active substances for commercial or experimental use. Accuracy and precision in the amount of liquid dispensed is important both from the standpoint of causing a desired reaction and minimizing the amount of materials used.

Equipment for dispensing microvolumes of liquid have been demonstrated with technologies such as those developed for ink jet applications. However, ink jet equipment has the advantage of operating with a particular ink (or set of inks) of known and essentially fixed viscosity and other physical properties. Thus, because the properties of the ink being used are known and fixed, automatic ink jet equipment can be designed for the particular ink specified. Direct use of ink jet technology with liquids containing a particular chemical and biological substance of interest ("transfer liquid") is more problematic. Such transfer liquids have varying viscosity and other physical properties that make accurate microvolume dispensing difficult. Automatic microvolume liquid handling systems should be capable of handling liquids of varying viscosity and other properties to accommodate the wide range of substances they must dispense. Another aspect of this problem is the need to accommodate accurately dispensing smaller and smaller amounts of transfer liquid. Especially in the utilization and test of biological materials, it is desirable to reduce the amount of transfer liquid dispensed in order to save costs or more efficiently use a small amount of material available. It is often both desirable and difficult to accurately dispense microvolumes of transfer liquid containing biological materials. Knowing the amount of transfer liquid dispensed in every ejection of transfer liquid would be advantageous to an automated system.

Another difficulty with dispensing microvolumes of transfer liquid arises due to the small orifices, e.g., 20–80 micrometers in diameter, employed to expel a transfer liquid. These small orifice sizes are susceptible to clogging. Heavy use of the nozzle promotes undesirable clogging by materials in the liquid being dispensed. Further exacerbating the clogging problem are the properties of the substances sometimes used in the transfer liquid. Clogging of transfer liquid substances at the orifice they are expelled from, or in other parts of the dispenser, can halt dispensing operations or make them far less precise. Therefore, it would be desirable to prevent or minimize clogging, be able to detect when such conditions are occurring, and to be able to automatically recover from these conditions. Failure of a microvolume dispenser to properly dispense transfer liquid can also be caused by other factors, such as air or other compressible gases being trapped in the dispensing unit. It would be desirable to detect and indicate when a microvolume dispenser is either not dispensing at all, or not dispensing the desired microvolume ("misfiring").

Over time it may be necessary to aspirate a variety of different liquid mixtures or solutions into the microvolume dispenser in order to dispense those liquids. Because each liquid may contaminate the microvolume dispenser with regard to a later-used liquid it is desirable to thoroughly clean a microdispenser when liquids are changed. Even when liquids are not changed, cleaning is necessary to prevent buildup of materials inside the microvolume dispenser. Unfortunately, using a pump alone to flush out the microvolume dispenser is not always 100% effective. Therefore, it would be desirable to be able to easily and thoroughly clean the microvolume dispenser from time to time.

In order to achieve an automated microvolume dispensing system it would be desirable to ensure in realtime that the transfer liquid is within some given range of relevant system parameters in order to rapidly and accurately dispense transfer liquid droplets of substantially uniform size. For example, it is desirable to ensure that the transfer liquid is accurately deposited at its target surface. Because industry requires rapid dispensing of microvolume amounts of transfer liquid, it is also desirable to be able to ascertain transfer liquid volume dispensed, and to be able to detect and recover from dispensing problems in realtime.

One object of the present invention to provide a microvolume liquid handling system which is capable of accurately verifying microvolume amounts of transfer liquid dispensed by sensing a corresponding change in pressure in the microvolume liquid handling system.

A further object of the present invention to provide a microvolume liquid handling system which can accurately measure an amount of dispensed liquid regardless of transfer liquid properties, such as, viscosity.

Another object of the present invention to provide a microvolume liquid handling system which can transfer microvolume quantities of liquids containing chemically or biologically active substances.

A further object of the present invention to provide a microvolume liquid handling system that prevents or minimizes clogging.

Still another object of the present invention to provide a microvolume liquid handling system which senses pressure changes associated with clogging and misfiring to indicate such improper operation.

Yet another object of the present invention to provide a microvolume liquid handling system which can verify that the transfer liquid is maintained within a given range of negative pressure (with respect to ambient atmospheric pressure) in order to accurately dispense microvolume amounts of transfer liquid and optimize the operation of the microdispenser.

A further object of the present invention to minimize the amount of transfer liquid that needs to be aspirated into the dispenser.

A still further object of the present invention to automatically detect when the dispenser tip enters and leaves the surface of the transfer liquid and/or wash liquid.

A still further object of the present invention is to provide for a real time detection of dispensing single drops of the transfer liquid.

Other objects and advantages of the present invention will be apparent to those skilled in the art upon studying of this application.

SUMMARY OF THE INVENTION

In accordance with one aspect of the present invention, a system of the present invention detects a pressure change resulting from ejection of a drop of a transfer liquid and generates an electrical signal indicating single drops of transfer liquid being dispersed in intervals measured by milliseconds. The dispersed drops being detected by the system can be in the range from about 5 picoliters to about 500 picoliters, preferably about 100 to about 500 picoliters. It has been discovered that by eliminating substantially all compressible fluids (gases) in the enclosed volume communicating with the ejection nozzle and containing the transfer liquid, the ejection of picoliter size drops can be detected by the present invention.

In accordance with another aspect of the present invention, it has been discovered that electrical signals indicating transient pressure changes in the transfer liquid upon dispensing of liquid drops in the range from about 5 picoliters to about 500 picoliters, preferably about 100 to about 500 picoliters can be detected even when the liquid in the enclosed volume of the dispenser is not fully enclosed, but is instead connected to a liquid reservoir. As long as substantially all compressible fluids (gases) are kept out of the dispensing conduit which communicates through a restricted passage to the liquid reservoir, the pressure sensor of the system of the present invention can detect dispensing of a single drop of liquid, having a size range from about 5 picoliters to about 500 picoliters, preferably 100 picoliters to about 500 picoliters. The pressure change resulting from ejection of such a drop returns to the pre-ejection pressure level in a time period long enough for the pressure change to be detectable but short enough to complete the cycle before the next drop is ejected. In the preferred embodiment, the drops were ejected within 10 milliseconds of each other and depending on the operating conditions the pressure returned to the normal level in the time range from about 5 to about 10 milliseconds.

In accordance with another aspect of the present invention clogging is prevented or minimized by pulsing the piezoelectric transducer at frequencies in the range from about 1 KHz to about 20 Khz. If the microdispenser is determined to be clogged by the control logic, frequencies close to the resonant frequency of the microdispenser are generally used, generally about 12 KHz. The piezoelectric transducer can also be pulsed at or near the resonant frequencies when the microdispenser is being cleaned. The resonant vibrations of the microdispenser during cleaning result in a cleaner microdispenser interior than without vibration. Because the same transducer is used to prevent clogging, to break up existing clogs and to clean the microdispenser, greater efficiencies are achieved than previously possible.

In accordance with still another aspect of the present invention enables the microdispensers to be positioned with a high degree of accuracy with regard to wells of a microtitre plate. Visible or infrared light is transmitted through a transparent bottom half of a microtitre plate containing wells organized in rows and columns. Light does not pass through the opaque top half of the microtitre plate. When a particular microdispenser is moved from a position above the opaque top half of the microtitre plate to a position above the transparent bottom half of the microtitre plate, light passes through the glass capillary in the microdispenser where it is detected by a photo detector in optical contact with the glass capillary. The photo detector generates electronic signals corresponding to the amount of light received. The signals from the photo detector are coupled to a computer which uses the signals to help locate and verify the position of the microdispenser.

In accordance with another aspect of the present invention, the liquid surface in a vessel is detected and the microdispenser orifice is located based on the change of the pressure which occurs when the orifice of the microdispenser is in communication with a liquid reservoir.

Other aspects of the present invention will become apparent to those skilled in the art upon studying this disclosure.

DETAILED DESCRIPTION OF THE INVENTION

Figure 1:
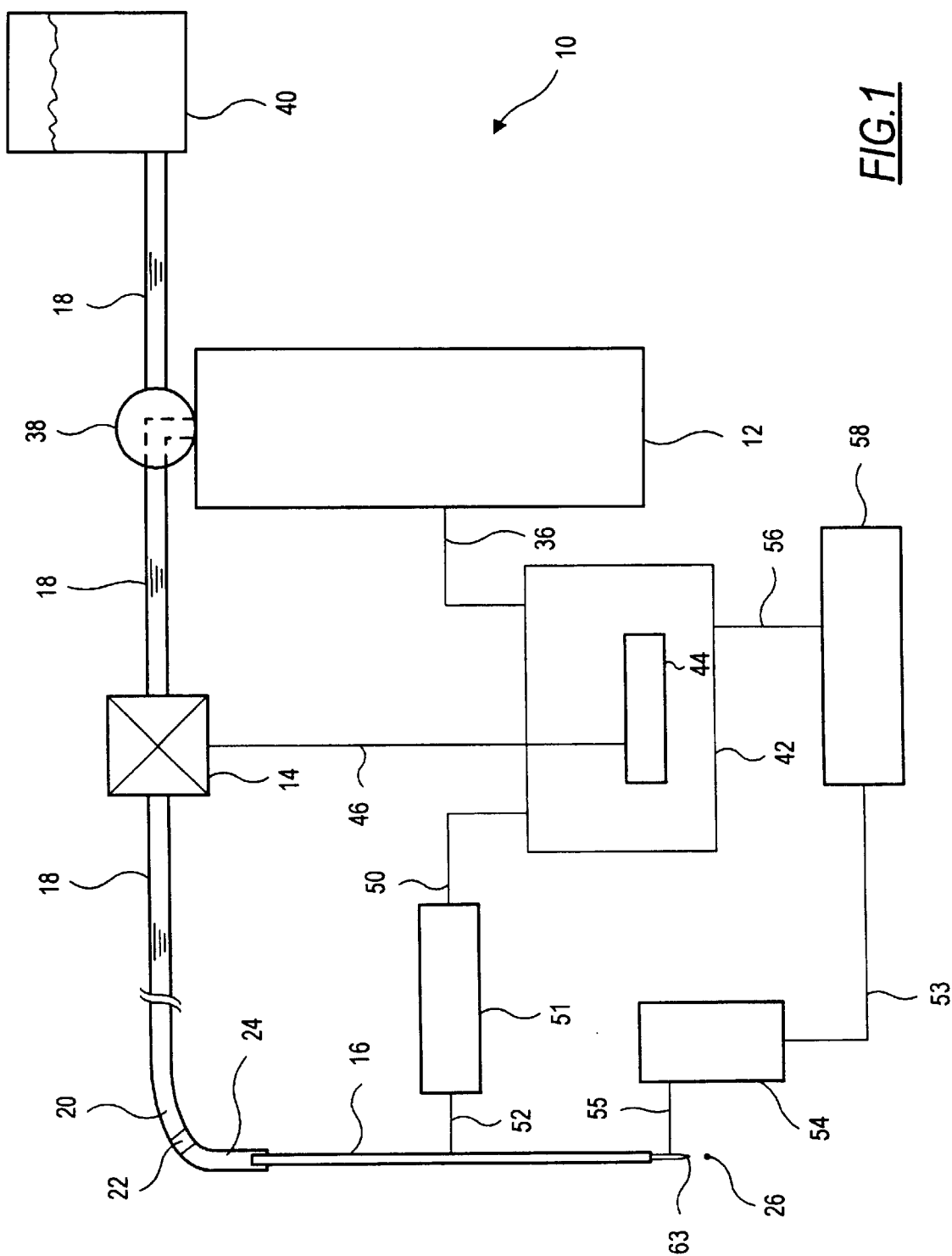
FIG. 1 is a block diagram of the a microvolume liquid handling system illustrating the first embodiment of the present invention.

The system of the present invention possesses unique capabilities in microvolume liquid handling. Surprisingly, it has been discovered that sub-nanoliter droplets of liquid can be dispensed with real time verification. Dispensing of a single sub-nanoliter drop can be detected in real time. As the result of dispensing the liquid in sub-nanoliter droplets, the dispensed volume can be precisely controlled. The dispenser of the present invention can automatically detect the liquid surface of the transfer liquid, automatically aspirate, analyze desired volume of the transfer liquid, dispense the transfer liquid without contacting the destination vessel or its contents, and automatically wash off the transfer liquid from dispensing system after each transfer. This system is capable of automatically sensing liquid surfaces, aspirating liquid to be transferred, and then dispensing small quantities of liquid with high accuracy, speed and precision. The system of the present invention is pulsated at high frequency to prevent or eliminate clogging. Immiscible liquids between the transfer liquid and the system liquid reduces the required amount of transfer liquid needed for dispensing.

DESCRIPTION OF THE FIRST PREFERRED EMBODIMENT

The system constructed in accordance with the first preferred embodiment of the present invention includes a system liquid and a transfer liquid separated by a known volume of gas, such as air, ("air gap") the air gap facilitates measuring small changes in pressure in the system liquid that correlate to the volume of transfer liquid dispensed. The transfer liquid contains the substances being dispensed, while one preferred system liquid is deionized water. Each time a droplet in the microvolume dispensing range is dispensed, the transfer liquid will return to its prior position inside the microdispenser because of capillary forces, and the air gap's specific volume will be increased corresponding to the amount of transfer liquid dispensed. This has the effect of decreasing pressure in the system liquid line which is measured with a highly sensitive piezoresistive pressure sensor. The pressure sensor transmits an electric signal to control circuitry which converts the electric signal into a digital form and generates an indication of the corresponding volume of transfer liquid dispensed. An advantage of the present invention is its insensitivity to the viscosity of the transfer liquid. This is because the pressure change in the system liquid corresponds to the microvolume dispensed, without being dependent on the viscosity of the dispensed liquid.

A first preferred embodiment by providing a microvolume liquid handling system which includes a positive displacement pump operated by a stepper motor, a piezoresistive pressure sensor, and an electrically controlled microdispenser that utilizes a piezoelectric transducer bonded to a glass capillary. The microdispenser is capable of rapidly and accurately dispensing sub-nanoliter ("nl") sized droplets by forcibly ejecting the droplets from a small nozzle, this is known as 'drop-on-demand'. Specifically, the dispenser of the present invention disperses drops in the range from about 5 picoliters to about 500 picoliters, preferably from about 100 picoliters to about 500 picoliters.

To provide the functionality of an automated liquid handling system, the microdispensers in all preferred embodiments are mounted onto a 3-axis robotic system that is used to position the microdispensers at specific locations required to execute the desired liquid transfer protocol.

Turning now to the drawings and referring first to FIG. 1, a first embodiment of microvolume liquid handling system 10 is illustrated. The microvolume liquid handling system 10 includes a positive displacement pump 12, a pressure sensor 14 and a microdispenser 16. Tubing 18 connects the positive displacement pump 12 to the pressure sensor 14 and the pressure sensor 14 to the microdispenser 16. The positive displacement pump 12 moves a system liquid 20 through the pressure sensor 14 and the microdispenser 16. After the system 10 is loaded with system liquid 20, an air gap 22 of known volume is provided. Then, an amount of transfer liquid 24 is drawn into the microdispenser 16 in a manner described below. The transfer liquid 24 can contain one or more biologically or chemically active substances of interest. Preferably, the microdispenser 16 expels (or synonymously, "shoots") sub-nanoliter size individual droplets 26 which are very reproducible. The expelled droplets 26 of transfer liquid 24 are generally in the range 5 to 500 picoliters, preferably 100 to 500 picoliters per droplet 26. For example, if one desires to expel a total of 9 nanoliters of transfer liquid 24, then the microdispenser 16 will be directed to expel 20 droplets 26, each having a volume of 0.45 nanoliters. Droplet 26 size can be varied by varying the magnitude and duration of the electrical signal applied to the microdispenser 16. Other factors affecting droplet size include: the size of the nozzle opening at the bottom of the microdispenser, the pressure at the microdispenser inlet, and properties of the transfer liquid.

Figure 2:
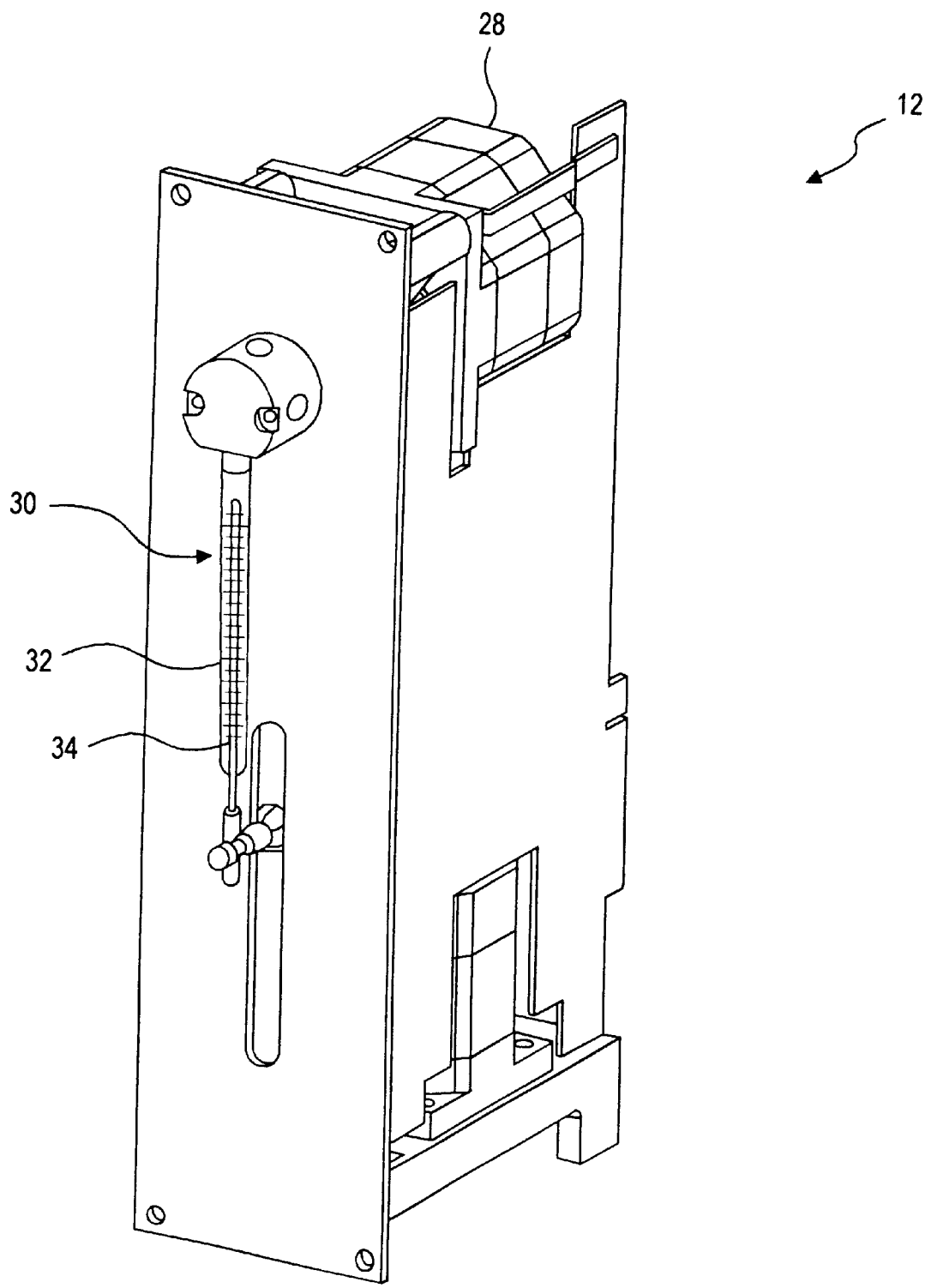
FIG. 2 is a schematic of a positive displacement pump illustrating an aspect of the first embodiment of the present invention.

Referring now to FIGS. 1 and 2, in one preferred embodiment the positive displacement pump 12 is a XL 3000 Modular Digital Pump manufactured by Cavro Scientific Instruments, Inc., 242 Humboldt Court, Sunnyvale, Calif. 94089. The positive displacement pump 12 includes stepper motor 28 and stepper motor 29, and a syringe 30. The syringe 30 includes a borosilicate glass tube 32 and a plunger 34 which is mechanically coupled through a series of gears and a belt (not shown) to the stepper motor 28. Stepper motor 28 motion causes the plunger 34 to move up or down by a specified number of discrete steps inside the glass tube 32. The plunger 34 forms a liquid-tight seal with the glass tube 32. In one preferred embodiment syringe 30 has a usable capacity of 250 microliters which is the amount of system liquid 20 the plunger 34 can displace in one full stroke. Depending on the selected mode of operation, the stepper motor 28 is capable of making 3,000 or 12,000 discrete steps per plunger 34 full stroke. In one preferred embodiment the stepper motor 28 is directed to make 12,000 steps per full plunger 34 stroke with each step displacing approximately 20.83 nanoliters of system liquid 20. In one preferred embodiment the system liquid 20 utilized is deionized water.

Digitally encoded commands cause the stepper motor 28 within the positive displacement pump 12 to aspirate discrete volumes of liquid into the microdispenser 16, wash the microdispenser 16 between liquid transfers, and to control the pressure in the system liquid 20 line for microvolume liquid handling system 10 operation. The positive displacement pump 12 is also used to prime the system 10 with system liquid 20 and to dispense higher volumes of liquid through the microdispenser 16, allowing dilute solutions to be made. The positive displacement pump 12 can also work directly with transfer liquid 24. Thus, if desired, transfer liquid 24 can be used as system liquid 20 throughout the microvolume liquid handling system 10.

To prime the microvolume liquid handling system 10, the control logic 42 first directs a 3-axis robotic system 58 through electrical wire 56 to position the microdispenser 16 over a wash station contained on the robotic system 58. In one preferred embodiment the microvolume liquid handling system 10 includes, and is mounted on, a 3-axis robotic system is a MultiPROBE CR10100, manufactured by Packard Instrument Company, Downers Grove, Ill. The positive displacement pump 12 includes a valve 38 for connecting a system liquid reservoir 40 to the syringe 30. An initialization control signal is transmitted through the electrical cable 36 to the pump 12 by control logic 42 which causes the valve 38 to rotate connecting the syringe 30 with the system liquid reservoir 40. The control signal also causes the stepper motor 28 to move the plunger 34 to its maximum extent up (Position 1 in FIG. 2) into the borosilicate glass tube 32. The next command from the control logic 42 causes the stepper motor 28 to move the plunger 34 to its maximum extent down (Position 2 in FIG. 2) inside the tube 32, to extract system liquid 20 from the system reservoir 40. Another command from the control logic 42 directs the valve 38 to rotate again, causing the syringe 30 to be connected with the tubing 18 connected to the pressure sensor 14. In one preferred embodiment the tubing 18 employed in the microvolume liquid handling system 10 is Natural Color Teflon Tubing made by Zeus Industrial Products, Inc., Raritan, N.J., with an inner diameter of 0.059 inches and an outer diameter of 0.098 inches. The next command from the control logic 42 to the positive displacement pump 12 causes the system liquid 20 inside of the syringe 30 to be pushed into the microvolume liquid handling system 10 towards the pressure sensor 14. Because the microvolume liquid handling system 10 typically requires about 4 milliliters of system liquid to be primed, the sequence of steps described above must be repeated about 16 times in order to completely prime the microvolume liquid handling system 10.

The control logic 42 receives signals from the pressure sensor 14 through an electrical line 46. The signals are converted from an analog form into a digital form by an A/D (analog to digital) converter 44 and used by the control logic 42 for processing and analysis. In one preferred embodiment the A/D conversion is a PC-LPM-16 Multifunction I/O Board manufactured by National Instruments Corporation, Austin, Tex. At various points in the liquid transfer process described herein, the control logic 42 receives signals from the pressure transducer 14, and sends command signals to the pump 12, microdispenser electronics 51, and the 3-axis robotic system 58. Within the control logic 42 are the encoded algorithms that sequence the hardware (robotic system 58, pump 12, and microdispenser electronics 51) for specified liquid transfer protocols as described herein. Also within the control logic 42 are the encoded algorithms that process the measured pressure signals to: verify and quantify microdispenses, perform diagnostics on the state of the microvolume liquid handling system, and automatically perform a calibration of the microdispenser for any selected transfer liquid 24.

The pressure sensor 14 senses fluctuations in pressure associated with priming the microvolume liquid handling system 10, aspirating transfer liquid 24 with pump 12, dispensing droplets 26 with microdispenser 16, and washing of microdispenser 16 using pump 12. In one preferred embodiment the pressure sensor 14 is a piezoresistive pressure sensor part number 26PCDFG6G, from Microswitch, Inc., a Division of Honeywell, Inc., 11 West Spring Street, Freeport, Ill. 61032. Also included with the pressure sensor 14 in the block diagram in FIG. 1 is electrical circuitry to amplify the analog pressure signal from the pressure sensor. The pressure sensor 14 converts pressure into electrical signals which are driven to the A/D converter 44 and then used by the control logic 42. For example, when the microvolume liquid handling system 10 is being primed, the pressure sensor 14 will send electrical signals which will be analyzed by the control logic 42 to determine whether they indicate any problems within the system such as partial or complete blockage in the microdispenser 16.

Once the microvolume liquid handling system 10 is primed, the control logic 42 sends a signal through electrical wire 56 which instructs the robotic system 58 to position the microdispenser 16 in air over the transfer liquid 24. The control logic 42 instructs stepper motor 28 to move the plunger 34 down, aspirating a discrete quantity of air (air gap), e.g., 50 microliters in volume into the microdispenser 16. The control logic 42 then instructs the robotic system 58 to move the microdispenser 16 down until it makes contact with the surface of the transfer liquid 24 (not shown) is made. Contact of the microdispenser 16 with the surface of the transfer liquid 24 is determined by a capacitive liquid level sense system (U.S. Pat. No. 5,365,783). The microdispenser is connected by electrical wire 55 to the liquid level sense electronics 54. When the liquid level sense electronics 54 detects microdispenser 16 contact with transfer liquid 24 surface, a signal is sent to the robotic system 58 through electrical wire 53 to stop downward motion.

The control logic 42 next instructs the pump 12 to move the plunger 34 down in order to aspirate transfer liquid 24 into the microdispenser 16. The pressure signal is monitored by control logic 42 during the aspiration to ensure that the transfer liquid 24 is being successfully drawn into the microdispenser 16. If a problem is detected, such as an abnormal drop in pressure due to partial or total blockage of the microdispenser, the control logic 24 will send a stop movement command to the pump 12. The control logic 24 will then proceed with an encoded recovery algorithm. Note that transfer liquid 24 can be drawn into the microvolume liquid handling system 10 up to the pressure sensor 14 without threat of contaminating the pressure sensor 14. Additional tubing can be added to increase transfer liquid 24 capacity. Once the transfer liquid 24 has been aspirated into the microdispenser 16, the control logic 42 instructs the robotic system 58 to reposition the microdispenser 16 above the chosen target, e.g., a microtitre plate.

In one preferred embodiment the microdispenser 16 is the MD-K-130 Microdispenser Head manufactured by Microdrop, GmbH, Muhlenweg 143, D-22844 Norderstedt, Germany.

Figure 3:
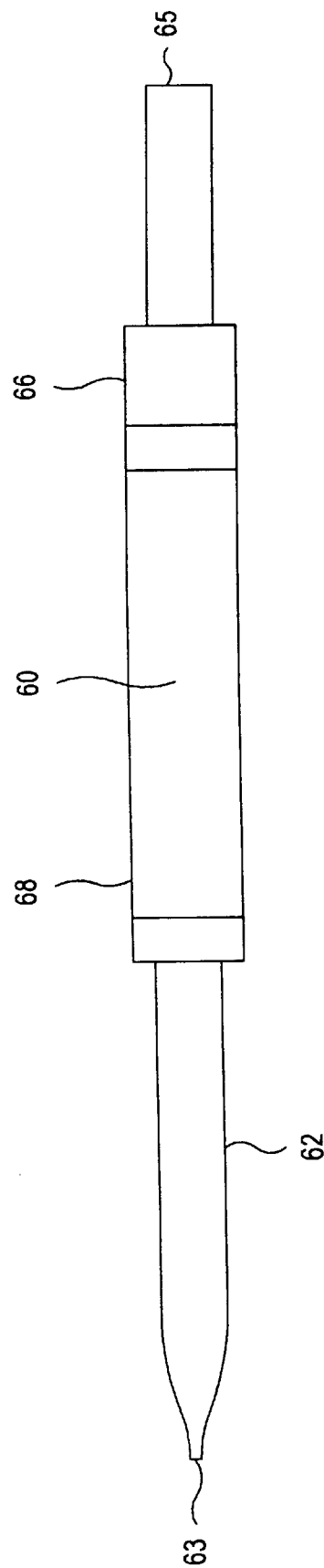
FIG. 3 is side plan view of a microdispenser including a piezoelectric transducer.

As illustrated in FIG. 3, the microdispenser 16 consists of a piezoceramic tube 60 bonded to a glass capillary 62. The piezoceramic tube has an inner electrode 66 and an outer electrode 68 for receiving analog voltage pulses which cause the piezoceramic tube to constrict. Once the glass capillary 62 has been filled with transfer liquid 24, the control logic 42 directs the microdispenser electronics 51 by electrical wire 50 to send analog voltage pulses to the piezoelectric transducer 60 by electrical wire 52. In one preferred embodiment the microdispenser electronics 51 is the MD-E-201 Drive Electronics manufactured by Microdrop, GmbH, Muhlenweg 143, D-22844 Norderstedt, Germany. The microdispenser electronics 51 control the magnitude and duration of the analog voltage pulses, and also the frequency at which the pulses are sent to the microdispenser 16. Each voltage pulse causes a constriction of the piezoelectric transducer 60, which in turn deforms the glass capillary 62. The deformation of the glass capillary 62 produces a pressure wave that propagates through the transfer liquid 24 to the microdispenser nozzle 63 where one droplet 26 of transfer liquid 24 is emitted under very high acceleration. The size of these droplets 26 has been shown to be very reproducible. The high acceleration of the transfer liquid 24 minimizes or eliminates problems caused by transfer liquid 24 surface tension and viscosity, allowing extremely small droplets 26 to be expelled from the nozzle, e.g., as small as 5 picoliter droplets 26 have been demonstrated. Use of the microdispenser 16 to propel droplets 26 out of the nozzle also avoids problems encountered in a liquid transfer technique called touchoff. In the touchoff technique, a droplet 26 is held at the end of the nozzle and is deposited onto a target surface by bringing that droplet 26 into contact with the target surface while it is still hanging off of the microdispenser 16. Such a contact process is made difficult by the surface tension, viscosity and wetting properties of the microdispenser 16 and the target surface which lead to unacceptable volume deviations. The present invention avoids the problems of the contact process because the droplets 26 are expelled out of the microdispenser 16 at a velocity of several meters per second. The total desired volume is dispensed by the present invention by specifying the number of droplets 26 to be expelled. Because thousands of droplets 26 can be emitted per second from the microdispenser 16, the desired microvolume of transfer liquid 24 can rapidly be dispensed.

In one preferred embodiment, the lower section of the glass capillary 62, between the piezoelectric transducer 60 and the nozzle 63, is plated with a conductive material, either platinum or gold. This provides an electrically conductive path between the microdispenser 16 and the liquid level sense electronics 54. In one preferred embodiment the glass capillary 62 has an overall length of 73 millimeters, and the nozzle 63 has an internal diameter of 75 micrometers.

Figure 4:
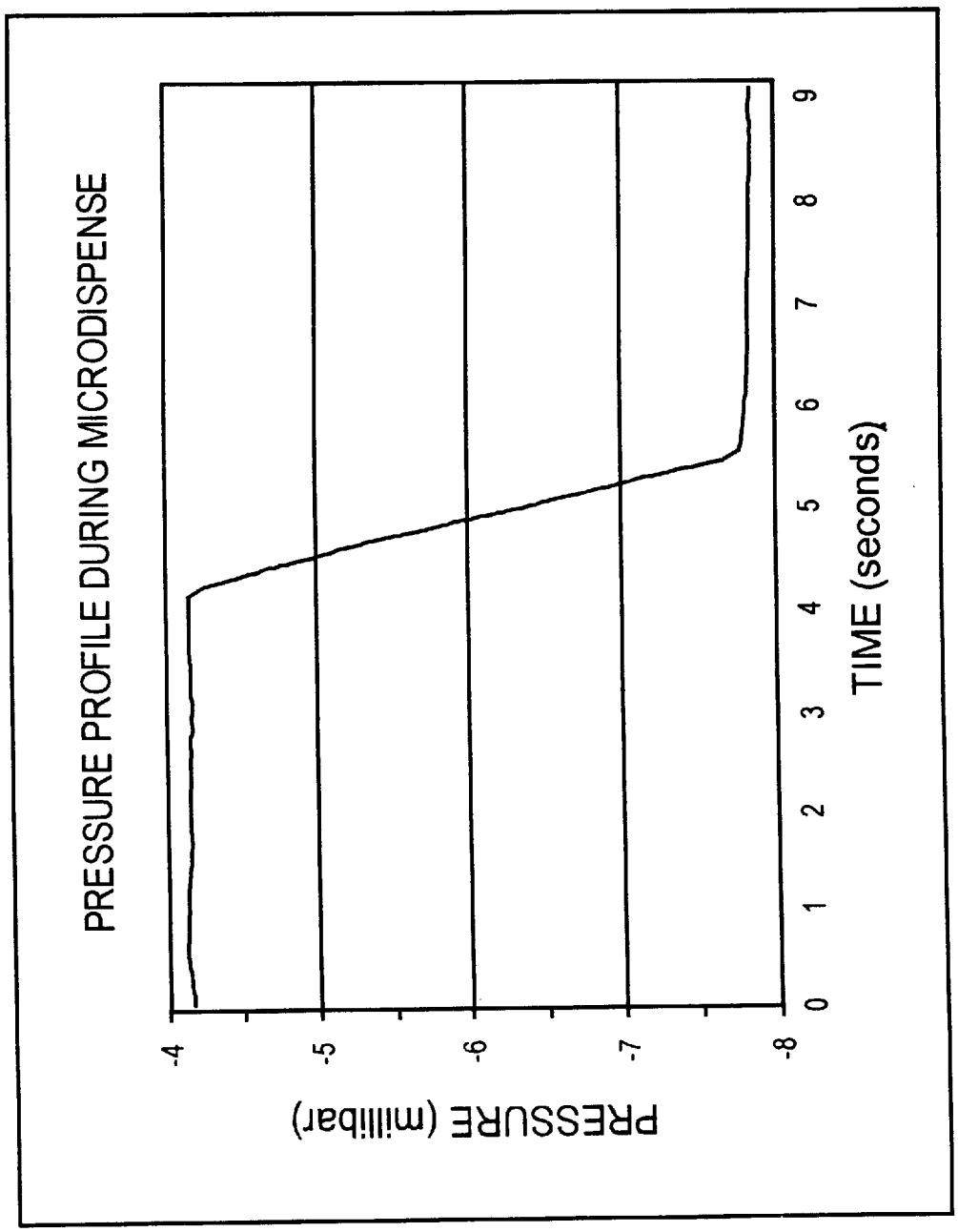
FIG. 4 is a graph depicting the system pressure measured during dispensing of microvolume of a liquid using a microdispenser of the present invention.

To dispense microvolume quantities of transfer liquid 24, analog voltage pulses are sent to the microdispenser 16, emitting droplets 26 of liquid. Capillary forces acting on the transfer liquid 24 replace the volume of transfer liquid 24 emitted from the microdispenser 16 with liquid from the tubing 18. However, since the transfer liquid-air gap-system liquid column terminates at a closed end in the positive displacement pump 12, there is a corresponding drop in the system liquid 20 line pressure as the air gap 22 is expanded. This is illustrated in FIG. 4 which depicts the pressure profile measured during a microdispense of 500 nanoliters. Important to the present invention, the magnitude of the pressure drop is a function of the size of the air gap 22 and the volume of the liquid dispensed.

With an air gap 22 of known volume, the pressure change as detected by the pressure sensor 14 relates to the volume dispensed. Thus, the control logic 42 determines from the pressure change measured by the pressure sensor 14, the volume of transfer liquid 24 that was dispensed. In one preferred embodiment of the present invention it is preferable that the drop in pressure not exceed approximately 30 to 40 millibars below ambient pressure, depending on the properties of the transfer liquid 24. If the amount of transfer liquid 24 dispensed is sufficient to drop the pressure more than 30 to 40 millibars, the pressure difference across the microdispenser 16, i.e., between the ambient pressure acting on the nozzle 63 and the pressure at the capillary inlet 63, will be sufficient to force the transfer liquid 24 up into the tubing 18. This will preclude further dispensing. There is a maximum amount of transfer liquid 24 that can be dispensed before the control logic 42 is required to command the pump 12 to advance the plunger 34 to compensate for the pressure drop. This maximum volume is determined by the desired dispense volume and the size of the air gap 22. Conversely, the size of the air gap 22 can be selected based on the desired dispense volume so as not to produce a pressure drop exceeding 30 to 40 millibars below ambient pressure. It is also within the scope of the present invention to advance the plunger 34 while the microdispenser 16 is dispensing, thereby rebuilding system liquid 20 line pressure, so that the microdispenser 16 can operate continuously.

The change in system liquid 20 pressure is used to determine that the desired amount of transfer liquid 24 was dispensed. A second verification of the amount of transfer liquid 24 that was dispensed is made by the control logic 42 monitoring the system liquid 20 line pressure while directing the pump 12 to advance the syringe plunger 34 upwards towards Position 1. The syringe plunger 34 is advanced until the system liquid 20 line pressure returns to the initial (pre-dispense) value. By the control logic 42 tracking the displaced volume the plunger 34 moves (20.83 nanoliters per stepper motor 28 step), a second confirmation of dispensed volume is made, adding robustness to the system. The system liquid 20 line pressure is now at the correct value for the next microdispenser 16 dispense, if a multi-dispense sequence has been specified.

Once the transfer liquid 24 dispensing has been completed, the control logic 24 causes the robotic system 58 to position the microdispenser 16 over the wash station. The control logic 24 then directs pump 12 and robotic system 58 in a wash sequence that disposes of any transfer liquid 24 left in the microdispenser 16, and washes the internal surface of glass capillary 62 and the external surface in the nozzle 63 area that was exposed to transfer liquid 24. The wash liquid can either be system liquid 20 or any other liquid placed onto the deck of the robotic system 58. The wash sequence is designed to minimize cross-contamination of subsequent transfer liquids 24 with transfer liquids processed prior. Toward this end, it is also possible to use a high frequency pulsing of the transducer 60 to facilitate washing of the microdispenser 16. This is accomplished by the control logic 42 directing the microdispenser electronics 51 to send electrical pulses to the microdispenser at a frequency in the range from about 1 to 20 Khz, preferably 12–15 kilohertz (the preferred resonant frequency of the microdispenser 16 is believed to be approximately 12 kilohertz), that coincides with a resonant frequency of the microdispenser 16—transfer liquid 24 system. Pulsing the piezoelectric transducer 60 at the above frequencies causes the interior surfaces of the glass capillary 62 to vibrate vigorously. In both the first and third embodiments, system liquid 20 or a special cleaning and/or neutralizing liquid is used to flush out the microdispenser 16 while the piezoelectric transducer 60 is activated at frequencies. Cleaning with pulsing at high frequencies has the effect of far more efficiently dislodging and eliminating matter adhering to the microdispenser 16. For example, it has been shown in a number of test cases that such cleaning caused a 200% to 500% improvement (depending on the contaminant) in the reduction of residual matter left in the microdispenser 16 as compared to cleaning without such pulsing.

Pulsing of the microdispenser 16 also is used to prevent, minimize or alleviate clogging of the nozzle of the microdispenser. For example, when transfer liquid is being aspirated into the microdispenser 16 it must pass through the relatively narrow nozzle 63 in the glass capillary 62. Matter in the transfer liquid 24 often comes into contact with the nozzle's 63 surfaces permitting the matter to adhere to the nozzle 63, depending on the nature of the contact. In biochemical applications, one widely used matter added to the transfer liquid 24 is polystyrene spheres. These spheres typically range from 1 $\mu M$ to over 30 $\mu M$ and may be uncoated or coated with magnetic ferrites, antigens or other materials. The relatively large size of the polystyrene spheres with regard to nozzle 63 diameter, in combination with their sometimes sticky coatings, can cause the spheres to adhere to the nozzle 63. It has been discovered that if the piezoelectric transducer 60 is excited at high frequency of the microdispenser 16 while the microdispenser 16 is being loaded (i.e. transfer liquid 24 is being aspirated in to the microdispenser 16) that clogging is prevented or less likely to occur. Thus, high frequency pulsing of the microdispenser 16 works to prevent or diminish clogging of the nozzle 63 by materials in the transfer liquid 24.

Anytime a transfer liquid 24 containing dissolved or suspended materials passes through the nozzle 63 there is a possibility of clogging. Accordingly, not only is clogging a problem during aspiration of transfer liquid 24 into the microdispenser 16 as described above, but it is also a problem when transfer liquid is dispensed from the high frequency pulsing of the microdispenser 16 between droplet dispensing by the piezoelectric transducer can reduce buildup of materials adhering to the nozzle 63 and thus prevent clogging in some instances. Even if substantial clogging does occur, high frequency pulsing of the microdispenser 16 by the piezoelectric transducer 60 will substantially clear the clogging materials from the nozzle 63. The key advantage here is that by preventing or eliminating clogging of the nozzle 63, the microvolume liquid handling system 10 can continue operation without resort to extraordinary cleaning procedures and the delays associated with those procedures. In short, system downtime is reduced, thereby making the microvolume liquid handling system 10 more efficient.

In the above description of the invention, the control of the microdispenser 16 was effected by sending a specific number of electrical pulses from the microdispenser electronics 51, each producing an emitted droplet 26 of transfer liquid 24. It is also within the scope of the invention to control the microdispenser 16 by monitoring the pressure sensor 14 signal in realtime, and continuing to send electrical pulses to the microdispenser 16 until a desired change in pressure is reached. In this mode of operation, the PC-LPM-16 Multifunction I/O Board that contains the A/D converter 44 is instructed by control logic 42 to send electrical pulses to the microdispenser electronics 51. Each pulse sent by the Multifunction I/O Board results in one electrical pulse that is sent by the microdispenser electronics 51 to the microdispenser 16, emitting one droplet 26 of transfer liquid 24. The control logic 42 monitors the pressure sensor 14 signal as the microdispenser 16 dispense is in progress, and once the desired change is pressure has been attained, the control logic 42 directs the Multifunction I/O Board to stop sending electrical pulses.

This mode of operation is employed if a "misfiring" of microdispenser 16 has been detected by control logic 42.

It is also within the scope of the invention for the microvolume liquid handling system 10 to automatically determine (calibrate) the size of the emitted droplets 26 for transfer liquids 24 of varying properties. As heretofore mentioned, emitted droplet 26 size is affected by the properties of the transfer liquid 24. Therefore, it is desirable to be able to automatically determine emitted droplet 26 size so that the user need only specify the total transfer volume, and the system 10 will internally determine the number of emitted droplets 26 required to satisfy the user request. In the encoded autocalibration algorithm, once the system 10 is primed, an air gap 22 and transfer liquid 24 aspirated, the control logic 42 instructs microdispenser electronics 51 to send a specific number of electrical pulses, e.g., 1000, to the microdispenser 16. The resulting drop in pressure sensor 14 signal is used by control logic 42 to determine the volume of transfer liquid 24 that was dispensed. This dispensed volume determination is verified by the control logic 42 tracking the volume displaced by the movement of the plunger 34 to restore the system liquid 20 line pressure to the pre-dispense value.

The microvolume liquid handling system 10 illustrated is FIG. 1 depicts a single microdispenser 16, pressure sensor 14, and pump 12. It is within the spirit and scope of this invention to include embodiments of microvolume liquid handling systems that have a multiplicity (e.g., 4, 8, 96) of microdispensers 16, pressure sensors 14, and pumps 12. It is also within the spirit and scope of this invention to include embodiments of microvolume liquid handling systems that have a multiplicity of microdispensers 16, pressure sensors 14, valves 38, and one or more pumps 12.

Second Preferred Embodiment

Figure 5:
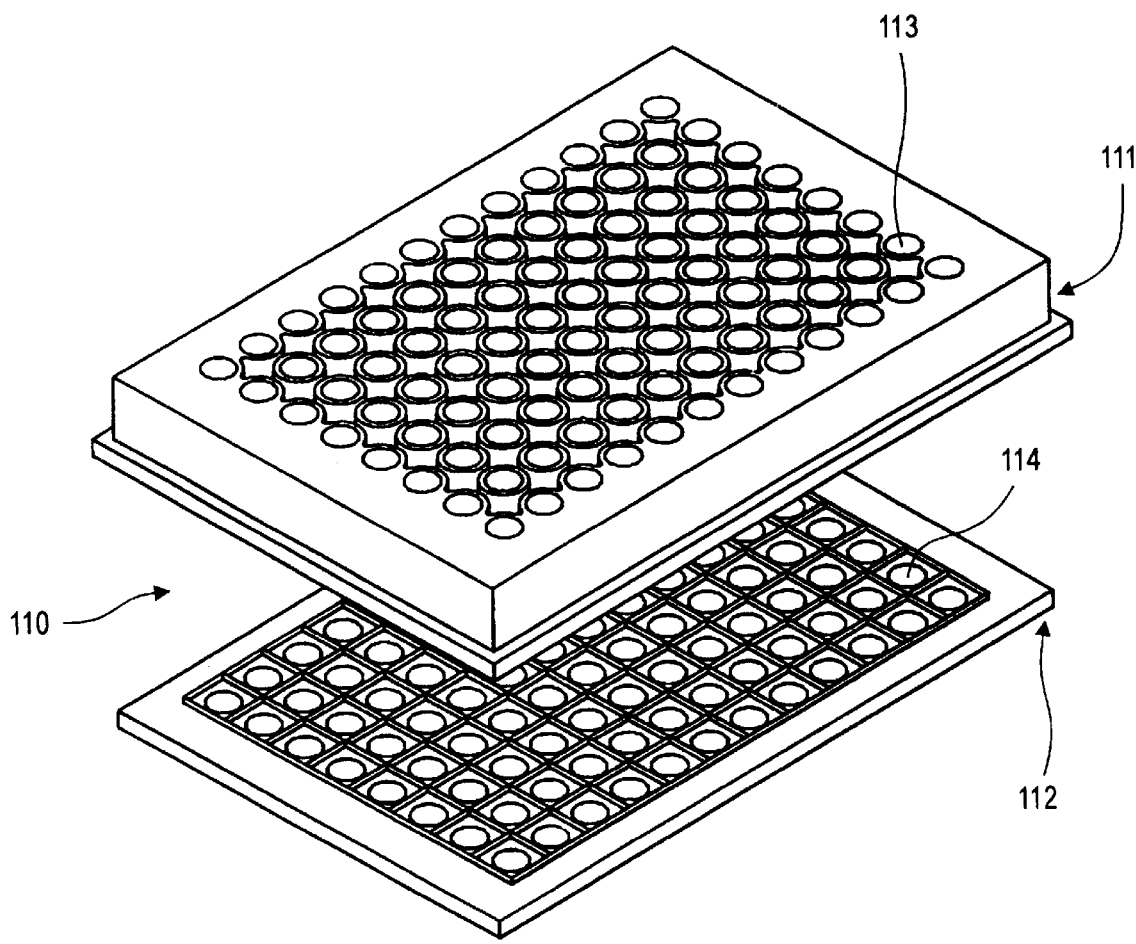
FIG. 5 is an exploded perspective view of two halves of a microtitre plate prior to being joined, as used with the present invention.
Figure 6:
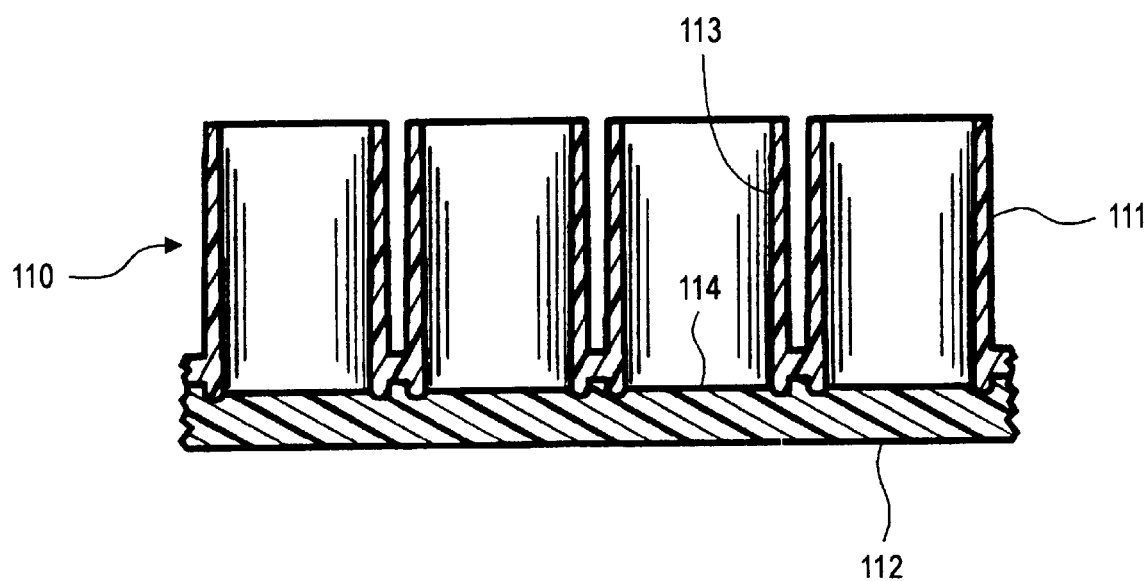
FIG. 6 is a sectional side plan view showing the two halves of the microtitre plate after having been joined in accordance with the present invention.

Turning now to FIGS. 5 and 6, one application for drop-on-demand microvolume liquid dispensing is to deposit precise amounts of transfer liquid 24 into an array of wells in a microtitre plate 110, which is described in U.S. Pat. No. 5,457,527, hereby incorporated by reference. The microtitre plate 110 is formed from two molded plastic plates 111 and 112. The upper plate 111 forms the side walls 113 of the multiple wells of the microtitre plate, and in the illustrative example, the wells are arranged in an 8×12 matrix, although matrices with other dimensions also work with the present invention. The bottom plate 112 forms the bottom walls 114 of the matrix web, and is attached to the lower surface of to the lower surface of the upper plate by fusing the two plates together. The upper plate 111 is formed from an opaque polymeric material so that light cannot be transmitted through. In contrast to the upper plate 111, the lower plate 112 is formed of a transparent polymeric material so that it forms a transparent bottom wall 114 for each sample well. This permits viewing of sample material through the bottom wall 114, and also permits light emissions to be measured through the bottom wall. The transparent bottom walls 114 may also be used to expose the sample to light from an external excitation source, while leaving the tops of the wells unobstructed for maximum detection area.

In part because the present microvolume liquid dispensing system 10 can precisely dispense extremely small quantities of liquid, it is possible to utilize microtitre arrays 110 of correspondingly reduced dimensions. The difficulty of positioning the nozzle 63 directly over each well increases as the well diameter approaches the one millimeter range. In the case of a well diameter of one millimeter, it is desirable to position the nozzle 63 within 150 micrometers ("$\mu$M") of the center of the well to permit accurate droplet shooting. The present invention utilizes a transparent bottom portion 112 of the microtitre plate array 110, which allows visible and infrared light to pass through the bottom of the microtitre array 110 into the well formed by the opaque side walls 113 of the microtitre plate array 111 and the transparent bottom walls 114 of the transparent bottom array 112. In one embodiment infrared light is passed through the transparent bottom section 112 of the microtitre plate array 110 onto the glass capillary 62 of the microdispenser 16. The light received at the microdispenser 16 is passed through the glass capillary 62 to an appropriate infrared detector (not shown) mounted on the glass capillary 62. The infrared light source, in combination with the narrow well structure, provides a narrow beam of infrared light directed upward through each well, but not through an opaque material between the wells. As the microdispenser is moved from one well to another it encounters a relatively dark zone indicating the dispenser is between wells, followed by a relatively bright zone indicating the edge of the next well is directly below. The positioning robot then uses these cues to reach and verify the position of the microdispenser.

In another preferred embodiment, visible light is used in place of infrared light as described above. For example, any visible wavelength of light can be used if the wells are devoid of liquid, or have clear liquids and a matching detector is used in place of the infrared detector. In the case where a turbid or cloudy liquid is present in the wells, a greenish light at 300 nM can be passed through the microtitre plate 110 to the turbid liquid. A cryptate compound added to the liquid present in the well fluoresces in response to excitation by the greenish light. Cryptate fluoresces at approximately 620 and 650 nM, corresponding to red light. A detector that detects those red wavelengths is used in place of the infrared detector.

Third Preferred Embodiment

Figure 7:
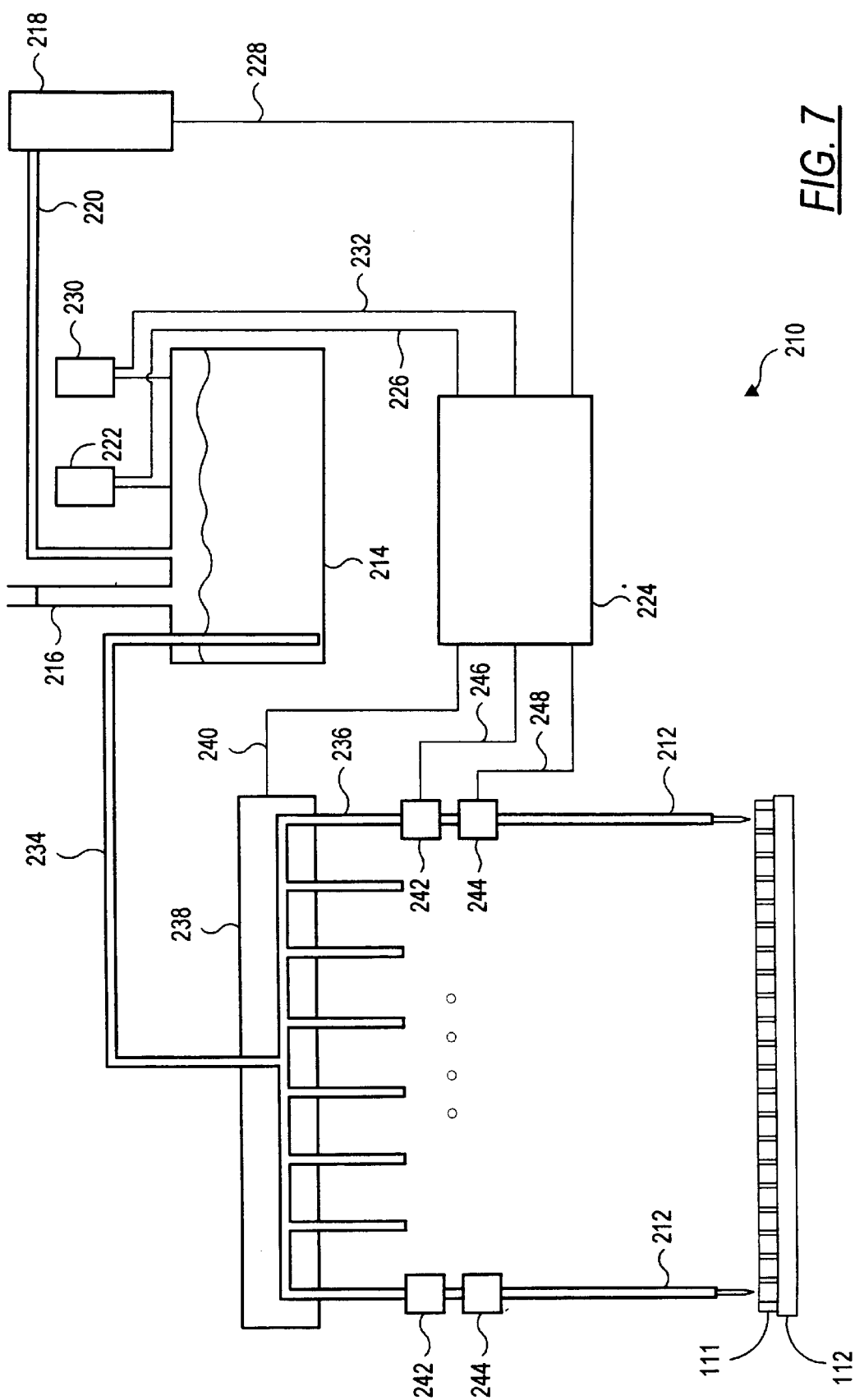
FIG. 7 is a block diagram of the a microvolume liquid handling system illustrating the second embodiment of the present invention.

Turning now to FIG. 7, another preferred embodiment of the microvolume liquid handling system 210 is shown. This preferred embodiment of the microvolume liquid handling system, which is more preferred than the first preferred embodiment when the number of microdispensers employed is equal to or greater than eight, also realizes the foregoing objectives. The third preferred embodiment is similar to the first preferred embodiment, except that the positive displacement pump (which includes a valve as described below), the stepper motor, and the piezoresistive pressure sensor are replaced with a pressure control system for supplying system liquid and controlling system liquid pressure, a plurality of flow sensors for detecting liquid flow as well as pressure in the system liquid present in connecting tubing coupled to each microdispenser, and plurality of valves (such as solenoid or microfabricated valves), each valve coupling each microdispenser to a system reservoir in the pressure control system. In this preferred embodiment, a system liquid reservoir 214 is used to supply system liquid 20 to all the microdispensers 212, thus eliminating the separate pump and pressure sensor for each microdispenser 212 in the first preferred embodiment. Note that first and third preferred embodiments are otherwise identical in structure and operation except as described herein. The precise number of microdispensers employed is a function of the user's dispensing requirements.

With regard to the third preferred embodiment, the system liquid reservoir 214 receives system liquid 20, typically deionized water or dimethyl sulfoxide (DMSO), through an intake tube 216 which contains a cap (not separately shown). The cap on the intake tube 216 is removed to enable the sealed system liquid reservoir 214 to receive system liquid 20 when the cap is off and seals the system liquid reservoir 214 shut when the cap is on so that the system liquid reservoir 214 can be maintained at a desired pressure. Pressure in the system liquid reservoir 214 is maintained by a pressure control system 218, through pressure control tubing 220. The pressure control system 218 includes an electrically controlled pump capable of accurately increasing or decreasing pressure in the system liquid reservoir 214. A pressure sensor 222 mounted on the system liquid reservoir 214 senses pressure in the system liquid reservoir 214 and transmits an electrical signal indicative of that pressure to a system controller 224 through electrical conductor 226. The system controller 224 contains a digital signal processor board and other electronics(not shown) which enable monitoring of various electrical signals, execution of control software code, and control of the microvolume liquid handling system 210. The system controller 224 electrically controls the pressure control system 218 through an electrical conductor 228 to adjust the pressure of the system liquid 20, and correspondingly, the pressure of the transfer liquid 24. A pressure relief valve 230 is mounted on the system liquid reservoir 214. The pressure relief valve 230 releases pressure from the system liquid reservoir 214 when the pressure exceeds a predetermined safety threshold. In one embodiment, the pressure relief valve 230 can also be opened by the system controller 224 which is connected to the pressure relief valve 230 by a wire 232.

During operations, the system controller 224 directs the pressure control system 218 to maintain one of three different pressure levels in the system reservoir 214 with regard to ambient atmospheric pressure. Each of the three pressure levels correspond to a different phase of operation of the microvolume liquid handling system 210. The three different pressure levels are a positive pressure, a high negative pressure and a low negative pressure. Prior to dispensing, the positive pressure level is used for cleaning in order to wash the microdispenser free of any foreign matter in combination with high frequency pulsing of the microdispensers 212 in the manner described above. After the microdispensers 212 are relatively clean, the high negative pressure level, roughly 200 millibars less than the ambient atmospheric pressure, is used to aspirate transfer liquid 24 into the microdispensers 212. Once the transfer liquid 24 has been aspirated into the microdispensers 212, the low negative pressure level, roughly −15 millibars, is used to supply back pressure to the transfer liquid 24 in the microdispensers 212 such that as droplets are dispensed, no additional transfer liquid 24 leaves the microdispensers 212.

System liquid 20 in the system reservoir 214 is coupled to the microdispensers 212 through a distribution tube 234 that splits into a plurality of sections 236 as shown in FIG. 7, one section 236 is connected to each microdispenser 212. Attached to each of the distribution tube sections 236 are solenoid valves 242 and flow sensors 244. The system controller 224 sends electrical signals through an electrical connection 246 to control the valves 242. A flow sensor 244 is attached to each distribution tube section 236 to determine the amount of liquid that is being aspirated into each microdispenser associated with that flow sensor 244. The flow sensor 244 detects flow of system liquid 20 into or out of each microdispenser 212. The flow sensors 244 are each connected to the system controller 224 through an electrical conductor 248. The electrical conductor 248 carries electrical signals from each flow sensor 244 indicating not only the amount of liquid flow, but also the pressure in each flow sensor. The flow sensors 244 are microfabricated which gives them the primary advantage of being sufficiently small so as to fit easily into the microvolume liquid handling system 210, for example the flow sensors 244 described in IEEE Proceedings, MEMS 1995, publication number 0-7803-2503-6, entitled, A Differential Pressure Liquid Flow Sensor For Flow Regulation and Dosing Systems, by M. Boillat et al., hereby incorporated by reference.

The distribution tube 234, which is physically connected to the microdispensers 212, is attached to a three axis robot 238, as in the first preferred embodiment, which correspondingly relocates the microdispensers 212 to positions above different microtitre plate 110 wells. After the desired number of droplets has been dispensed into each well, the robot 238 moves the microdispensers 212 to the next set of wells for further dispensing. Precise coordination of the robot's 238 movement is accomplished as described above with reference to the use of light passed through the bottom microtitre plate 112. Of course, the dispensing heads can be stationary and the robotic system can be used to locate the source and destination vessels, such as microtiter plates or glass slides.

It has been discovered that the ejection of individual drops of a transfer liquid in a size 100 to about 500 picoliter can be detected using the system of the present invention including a pressure detector. In order to detect dispensing of such drops, the transfer and system liquids must be substantially free of compressible gases, such as, air. As used herein, the term "substantially free of compressible gas" means that the level of compressible gas, if any, is low enough to allow the detection of a drop of liquid being ejected from the system. It has been discovered, that as the amount of compressible gas in the system increases, the ability to detect dispensing of the drop decreases until at a certain level of compressible gas, the system cannot detect dispensing of a drop of the transfer liquid.

In accordance with one embodiment of the present invention, the volume from the dispensing nozzle, which holds the transfer liquid to the valve (242 in FIG. 7), is substantially free of compressible gas and is entirely enclosed. It has been discovered that in this preferred embodiment of the present invention drops can be ejected from such closed volume until the presence in the volume is reduced to about minus 45 millibars gauge. At about minus 45 millibars gauge the vacuum interferes with the ejection of the drops.

In accordance with another embodiment of the present invention, the volume from the nozzle containing the transfer liquid to a reservoir of system liquid is substantially free of compressible fluid (gas). It has been discovered that upon dispensing of a drop of liquid, the system of this embodiment can detect a pressure change in the system liquid resulting from such drop being dispensed. The pressure change is transient in that as the transfer liquid flows into the volume adjacent to the nozzle replacing the ejected drop volume, the pressure rises to the level prior to the dispensing of the drop. It has been discovered that for dispensing drops in the size range from about 100 to about 500 picoliters, the time period for the pressure to reach the original level can be in a range from about 5 to about 10 milliseconds. This time period to return to the original pressure level can be controlled by selecting the size and the confirmation of the orifice between the volume adjacent to the nozzle and the reservoir. It has been determined that purging the air out of the system with a fluid (gas) that has a high solubility coefficient with the system liquid has greatly reduced the residual compressible fluid (gas) in the system after priming with system liquid. Once primed, keeping compressible fluids (air) out of the system is enhanced by degassing the system liquid, pressurizing the system liquid reservoir with an inert gas, utilizing low permeability tubing, and also degassing system liquid in-line. To aid in elimination of air bubbles, carbon dioxide purging can be employed as described in an article by R. Zengerle, M. Leitner, S. Kluge and A. Richter entitled "Carbon Dioxide Priming of Micro Liquid Systems" (0-7803-2503-6 copyright 1995 IEEE).

The system substantially as shown in FIG. 7 and as described herein was used to dispense drops of dimethyl sulfoxide (transfer liquid). The only difference in the structure of the system was that the microvalve 242 shown in FIG. 7 was replaced with a conventional solenoid valve 242 purchased under part number LHDA 1221111 from Lee Company of Westbrook, Conn. The system downstream of the reservoir 214 was entirely filled with dimethyl sulfoxide, with no air gaps in the system. The solenoid valve 242 was left open. During the run, voltage ranging from 40 volts to 95 volts applied to microdispenser 212 (which is shown in detail in FIG. 3). Specifically, pulse voltages to microdispenser, the device 212, were initially set at the following levels:

| MICRODISPENSER # | PULSE VOLTAGE (volts) |
|---|---|
| 1 | 90 |
| 2 | 90 |
| 3 | 90 |
| 4 | 85 |
| 5 | 40 |
| 6 | 95 |
| 7 | 95 |
| 8 | 90 |

Figure 8:
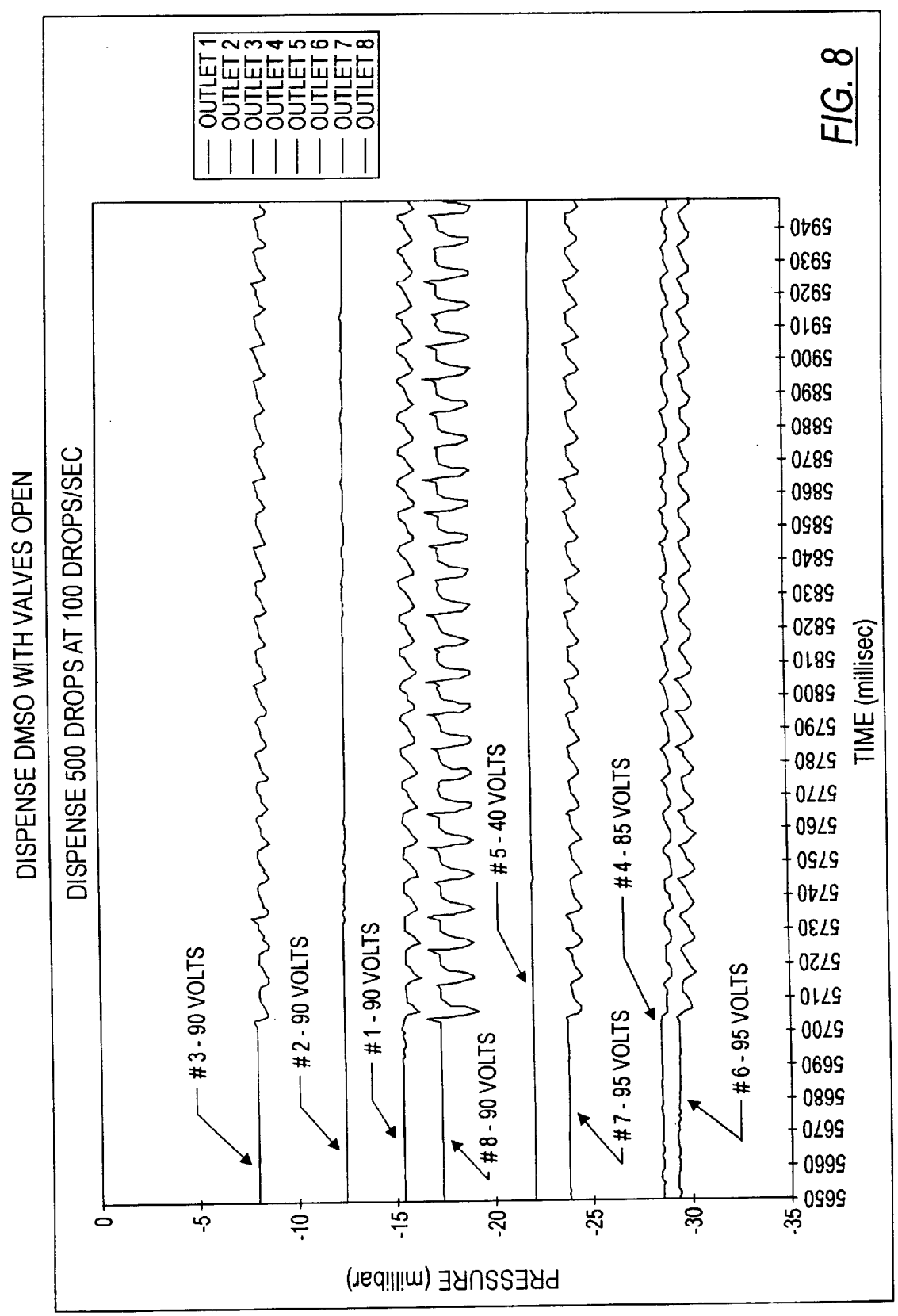
FIG. 8 is a plot of the pressure (in millibars) detected in eight dispenser heads as a function of time while dispensing drops of dimethyl sulfoxide at 100 drops per second with valves to the reservoir shown in FIG. 7 in an open position.
Figure 9:
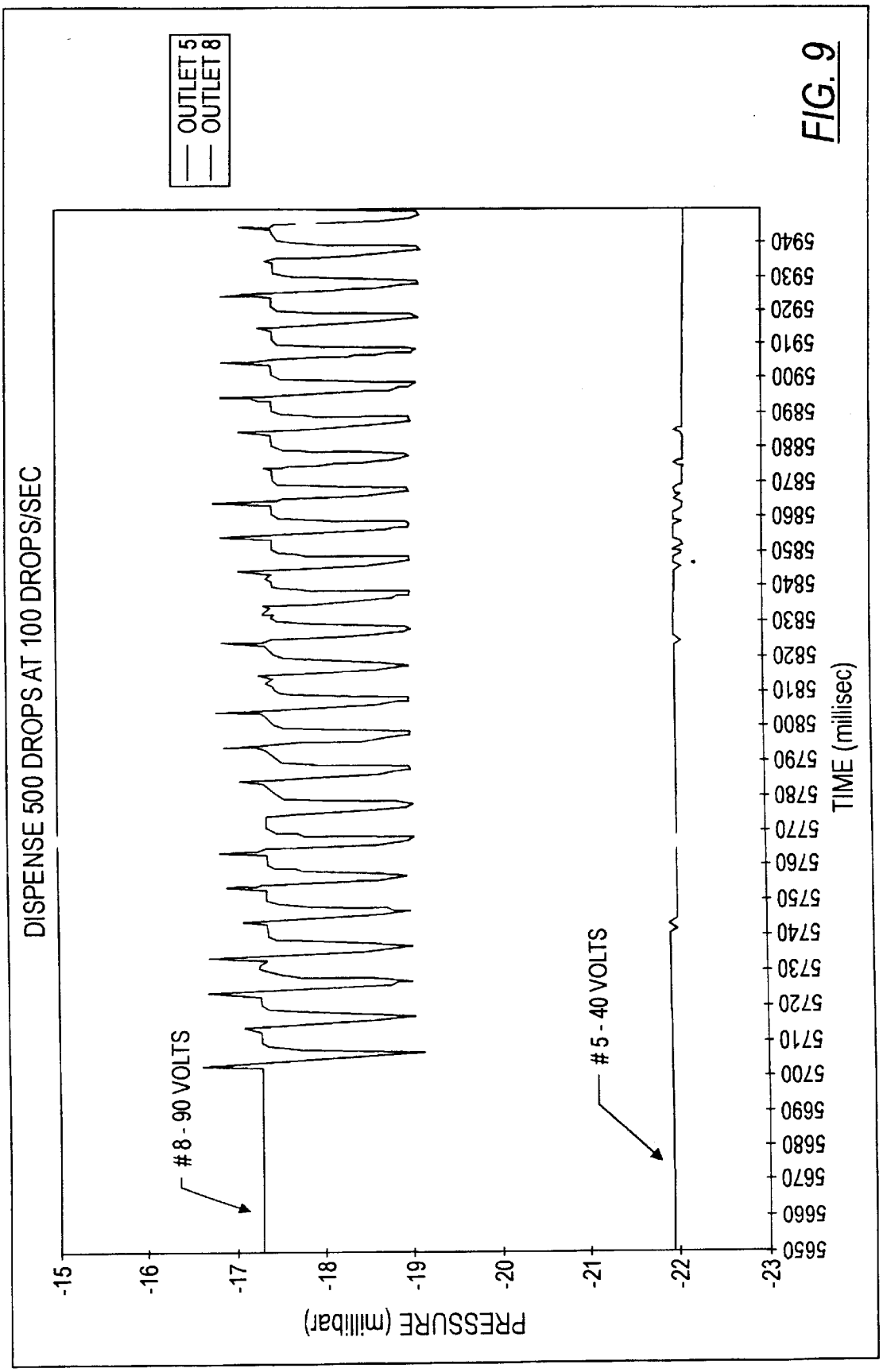
FIG. 9 is a plot the pressure (in millibars) detected in two of the dispensers shown in FIG. 8, on an expanded pressure scale.

As shown in FIGS. 8 and 9 drops were detected from all microdispensers except 2 and 5. The cause for microdispenser 2 not ejecting drops was determined to be due to an electrical short.

Figure 10:
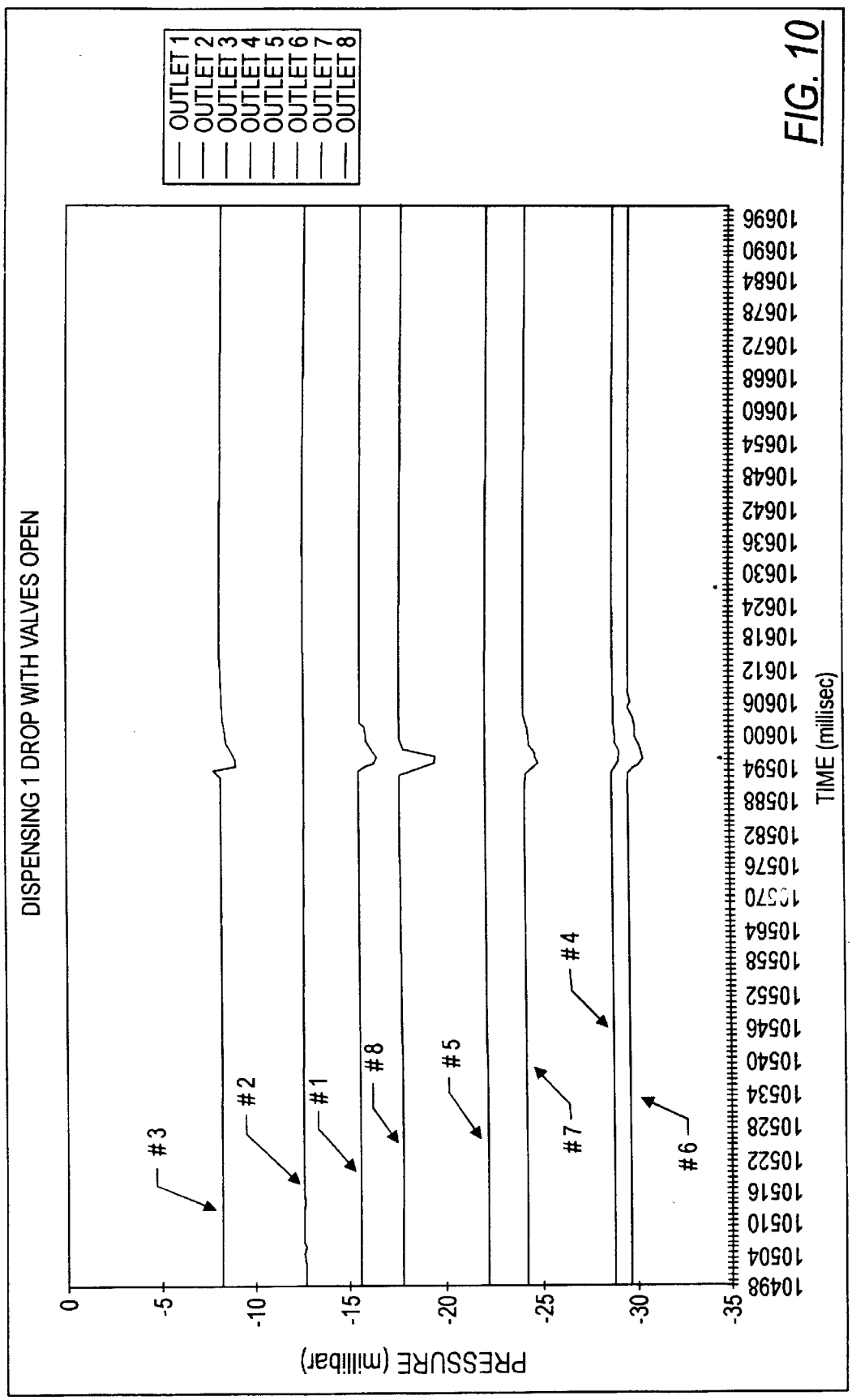
FIG. 10 is a plot of the pressure (in millibars) detected in eight dispenser heads as a function of time while dispensing a single drop of dimethyl sulfoxide with the valves to the reservoir shown in FIG. 7 in an open position.
Figure 11:
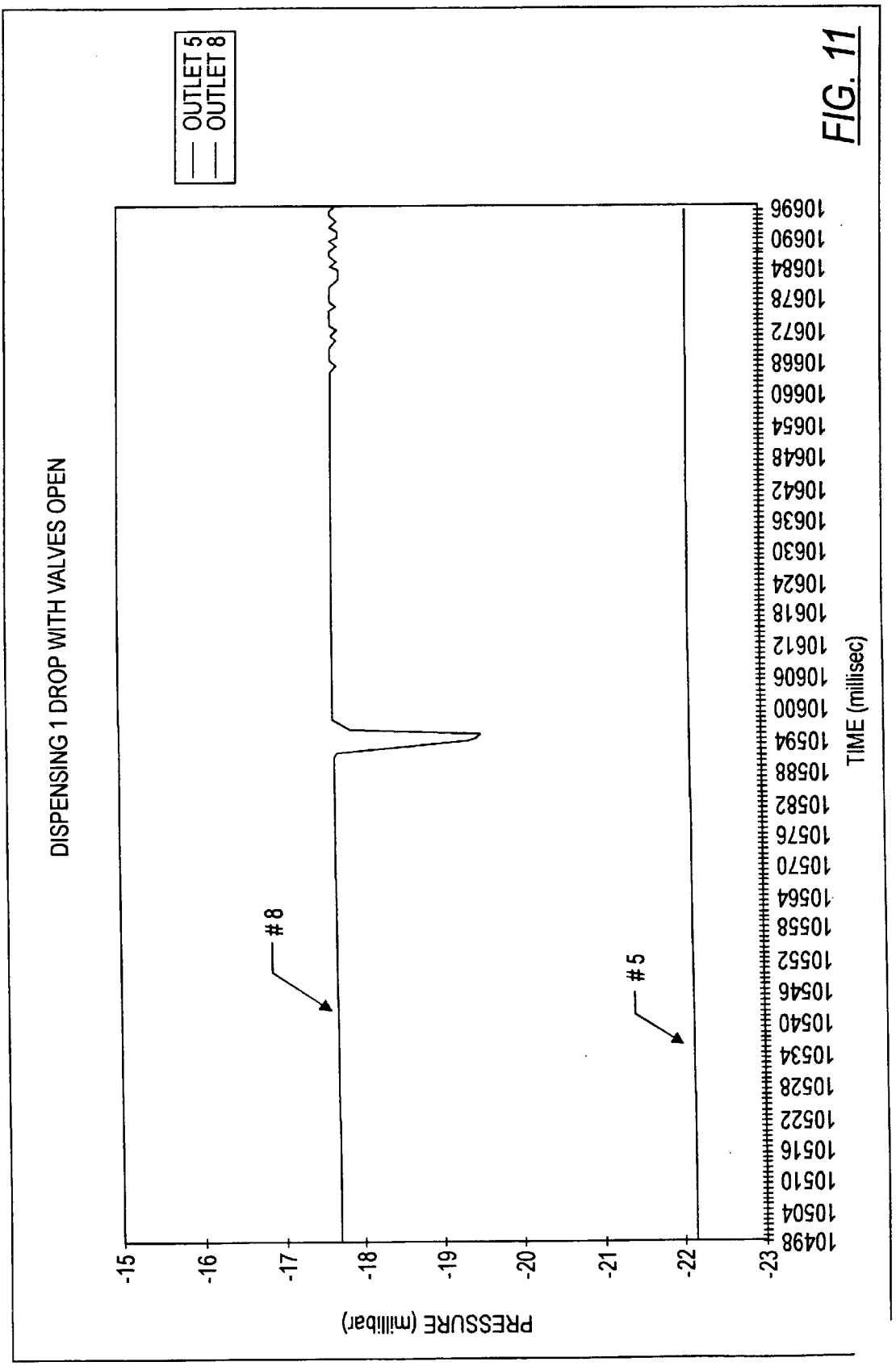
FIG. 11 is a plot showing the pressure (in millibars) detected in two of the dispensers shown in FIG. 10, on an expanded pressure scale.

The driven voltage for microdispenser 5 was purposely set low to not eject drops, and was used at a control for these tests. The same procedure was repeated with a single drop. The results of dispensing a single drop are shown in FIGS. 10 and 11. FIG. 11 shows the expanded version of the results for outlets 5 and 8 shown in FIG. 10.

In accordance with another aspect of the present invention, several methods have been developed to minimize the amount of transfer liquid that needs to be aspirated into the dispenser. In the system of the present invention, which is capable of monitoring the ejection of single drops, the dispensing chamber has to be free of compressible fluids (gas) in order for the drops to be ejected. This requires that the chamber from the nozzle (63 in FIG. 3) to the top of the piezoelectric transducer (60 in FIG. 3) be filled with liquid. This volume is often large in comparison to the volume of transfer liquid to be dispensed.

In accordance with one method, the system liquid and the transfer liquid are not separated from each other by an air gap as shown in FIG. 1. Instead, the two liquids are separated by a liquid which is immiscible with either or both the transfer liquid and the system liquid.

In accordance with another method to minimize the required aspirate volume of transfer liquid, system liquid is used to fill the dispenser before aspiration of the transfer liquid begins. The transfer liquid is then aspirated in direct contact with the system liquid. It has been discovered that the system liquid mixes with the transfer liquid at the interface slowly enough to allow dispensing of a large percentage of the transfer liquid without observing a dilution of the transfer liquid with the system liquid.

Of course, in embodiments which do not require use of a separate system liquid, a single liquid can be used to serve as both the system liquid and the transfer liquid. For example, it should be noted that in the experiments discussed in connection with FIGS. 8–11, dimethyl sulfoxide was employed as the only liquid, serving both as the system liquid and as the transfer liquid.

In accordance with a still further aspect of the present invention, the pressure in the dispenser (such as in dispenser 212 of FIG. 7) is reduced as the result of reducing the system liquid reservoir (214 in FIG. 7) pressure. The valve (242 in FIG. 7) is closed, and then the nozzle of the dispensing unit can be immersed in the transfer liquid to aspirate a small quantity of the transfer liquid into the dispenser. For example, when gauge pressure in the dispenser reaches minus 30 millibars, submersing the nozzle in the transfer liquid may draw a sufficient amount of liquid to increase the gauge pressure to minus 15 millibars. It should be noted that the dispenser does not aspirate air unless the surface tension in the nozzle is exceeded by the negative gauge pressure. In the preferred embodiment system using dimethyl sulfoxide, the negative gauge pressure to about 45 millibars does not produce air aspiration into the nozzle.

Fourth Preferred Embodiment

Figure 12:
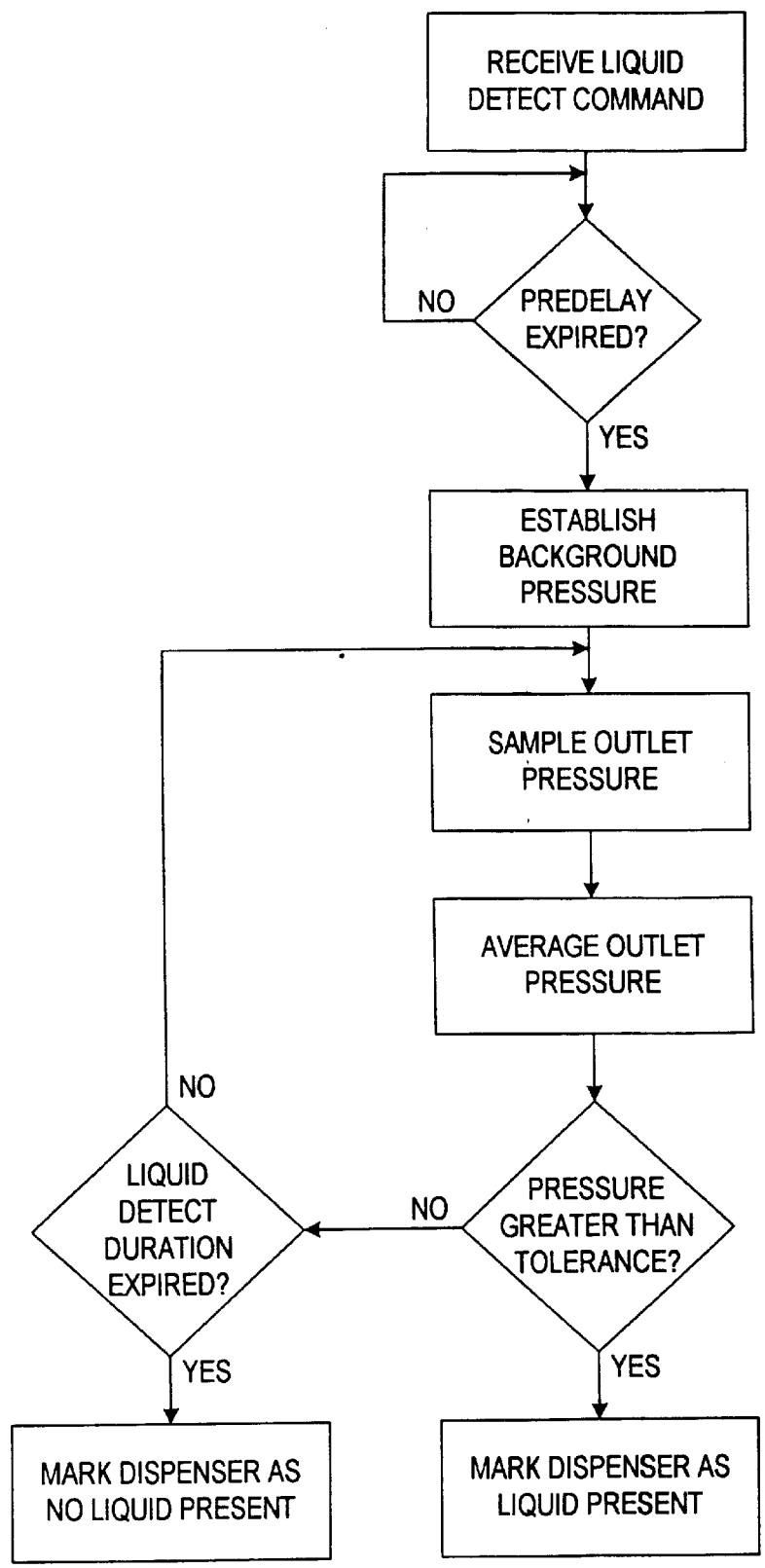
FIG. 12 is a block diagram of the program logic for operating pressure-based liquid detect feature of the present invention.

The system of the present invention can automatically detect when the microdispenser orifice enters into a liquid and when it is withdrawn. The block diagram of the program which carries out this automatic function is shown in FIG. 12.

A pressure-based liquid detect function has been developed for the 8 embodiments shown in FIGS. 1 and 7. This function can be used to detect when one or more micro dispensers have been placed into liquid, or withdrawn from liquid. This liquid/no liquid determination is made based on a pressure change which occurs when the microdispensers have been placed into liquid, or withdrawn from liquid. This pressure change is measured by monitoring the presure transducer, 14 in FIG. 1, or flow sensors, 244 in FIG. 7. This test is performed independently for each microdispenser in the system.

The liquid determination process can be divided into three distinct stages:

1. Predelay

Upon receipt of a "liquid level sense" command, the algorithm allows for a user-specified predelay to be performed. The software does nothing of significance during this time period, other than wait for the predelay to expire. This duration allows for some external event (i.e. the movement of the head to an aspiration source) to complete before the software begins to look for the pressure change characteristic of an air/liquid transition. Such movements may result in a false positive if they trigger a pressure change. Through this parameter, we are effectively telling the software to ignore any spurious pressure changes.

Note that the predelay can be zero, meaning that the software will begin monitoring the pressure immediately upon receipt of the "liquid level sense" command. This can also be applied in systems where the microdispensers are stationary, and the robotic system moves the source, or aspiration, vessel.

2. Baseline Establishment

Once the predelay has expired, baseline pressure value is established. The pressure is averaged over multiple readings. This baseline pressure value will then be compared to subsequent pressure readings to determine if they differ by enough to identify an air-liquid transition.

3. Liquid Detect

The last stage is to compare the established baseline pressure value with the current pressure values. The current pressure value is actually a rolling average, which ensures that a single spurious point will not result in an incorrect liquid detection event. During this stage, the pressure is read periodically. The oldest pressure value is then removed, newest pressure value added, and a new average calculated. This average is then compared with the baseline which was established in the previous stage. The difference between the baseline and the newly-established baseline is compared with a user-specified threshold value. If the magnitude of the difference is greater than the threshold, then the algorithm will conclude that a liquid detect event has occurred, and will set the liquid detected state to the control logic. The same test is performed independently for each dispenser.

The algorithm will continue to monitor for a liquid detect event until a user-specified detect duration has expired. If no pressure transition of the specified magnitude occurs during this duration, then the software will notify the control logic that no air-liquid transition has occurred for that particular dispenser.

The user-specified threshold value, in units of millibar, is used to fine-tune the liquid detect process. If true air-liquid transitions are occurring, but are not being identified, then the threshold value can be decreased, resulting in a more sensitive search. If false liquid-detect determinations are being made as a result of random pressure fluctuations, than the threshold value can be increased, resulting in a less sensitive liquid search. The threshold value also has a positive or negative sign associated with it, enabling the user to activate the liquid detect function either when immersing the microdispensers into liquid, or withdrawing them from liquid.

While the invention is susceptible to various modifications and alternative forms, specific embodiments thereof have been shown by way of example in the drawings and will herein be described in detail. It should be understood, however, that it is not intended to limit the invention to the particular forms disclosed. On the contrary, the intention is to cover all modifications, equivalents, and alternatives falling within the spirit and scope of the invention as defined by the appended claims.

What is claimed is:

1. A system for dispensing precise quantities of a transfer liquid, said system comprising:
   an enclosed space for holding fluids including said transfer liquid, a system liquid and a compressible fluid, said compressible fluid separating said transfer liquid from said system liquid said enclosed space having an outlet;
   means for supplying said system liquid into said enclosed space;
   means for introducing said compressible fluid into said enclosed space adjacent to said system liquid;
   means for providing said transfer liquid into said enclosed space adjacent to said compressible fluid and on the other side of the said compressible fluid from said system liquid, such that said compressible fluid separates said system liquid from said transfer liquid; and said transfer liquid is between said outlet and said compressible fluid;
   means for dispensing a quantity of said transfer liquid out of said outlet without introducing any fluid into said enclosed space during dispensing;
   means for sensing pressure change in said enclosed space resulting from the volume of the transfer liquid being dispensed;
   means for converting said pressure change to the volume of the transfer liquid dispensed by said dispensing means.

2. A method for dispensing from an enclosed space having a dispensing port, precise quantities of a transfer liquid and determining the precise volume of the transfer liquid,
   (a) transferring into the enclosed space a system liquid;
   (b) supplying into the enclosed space a compressible fluid adjacent to said system liquid;
   (c) transferring into the enclosed space a transfer liquid on the other side from said system liquid such that the compressible fluid, separates said transfer liquid from said system liquid adjacent to said compressible fluid, said transfer liquid being adjacent to the dispensing port;
   (d) dispensing droplets of the transfer liquid through said dispensing port;

(e) sensing pressure change in the enclosed space resulting from the droplets being dispensed;

(f) converting the pressure change sensed in step (e) into volume of liquid dispensed.

3. A method of claim 2 wherein the pressure change sensed in (e) does not exceed about 30 to 40 millibars below ambient pressure.

4. A method for dispensing from an enclosed space having a dispensing port precise quantities of a transfer liquid, said method comprising the following steps:

(a) introducing into the enclosed space a system liquid;

(b) introducing into the enclosed space a compressible fluid;

(c) introducing into the enclosed space a transfer liquid such that said compressible fluid separates said system liquid from said transfer liquid, said dispensing liquid being adjacent to said dispensing port;

(d) dispensing a predetermined number of droplets of the transfer liquid through the dispensing port;

(e) sensing the pressure change in the enclosed space resulting from dispensing of the drops in step (d);

(f) converting the pressure change into the volume of the transfer liquid;

(g) comparing the volume of the liquid dispensed in step (d) with the volume of the predetermined number of droplets.

* * * * *

UNITED STATES PATENT AND TRADEMARK OFFICE
CERTIFICATE OF CORRECTION

PATENT NO.   : 6,422,431 B2
DATED        : July 23, 2002
INVENTOR(S)  : Pelc et al.

It is certified that error appears in the above-identified patent and that said Letters Patent is hereby corrected as shown below:

<u>Title page,</u>
Item [57], ABSTRACT,
Line 4, replace "aspiring" with -- aspirating --.
Line 16, replace "microdispenser" with -- microdispensers --
Line 20, replace "dispenser" with -- microdispenser --

Signed and Sealed this

Fourth Day of February, 2003

JAMES E. ROGAN
*Director of the United States Patent and Trademark Office*